(12) United States Patent
Bagaoisan et al.

(10) Patent No.: US 11,707,265 B2
(45) Date of Patent: Jul. 25, 2023

(54) APPARATUS AND METHODS FOR SEALING A VASCULAR PUNCTURE

(71) Applicant: ACCESS CLOSURE, INC., Santa Clara, CA (US)

(72) Inventors: Celso J. Bagaoisan, Union City, CA (US); Sieu Duong, Campbell, CA (US)

(73) Assignee: ACCESS CLOSURE, INC., Santa Clara, CA (US)

( * ) Notice: Subject to any disclaimer, the term of this patent is extended or adjusted under 35 U.S.C. 154(b) by 531 days.

(21) Appl. No.: 16/827,702

(22) Filed: Mar. 23, 2020

(65) Prior Publication Data
US 2020/0375582 A1 Dec. 3, 2020

Related U.S. Application Data

(60) Division of application No. 14/191,237, filed on Feb. 26, 2014, now Pat. No. 10,595,838, which is a
(Continued)

(51) Int. Cl.
*A61B 17/00* (2006.01)
(52) U.S. Cl.
CPC ............ *A61B 17/0057* (2013.01); *A61B 2017/00557* (2013.01); *A61B 2017/00601* (2013.01);
(Continued)
(58) Field of Classification Search
CPC ...... A61B 17/0057; A61B 2017/00575; A61B 2017/00623; A61B 2017/00654;
(Continued)

(56) References Cited

U.S. PATENT DOCUMENTS 2,115,492 A 4/1938 Kober
2,365,039 A 12/1944 Andresen
(Continued)

FOREIGN PATENT DOCUMENTS

EP 0476178 A1 3/1992
EP 0482350 A2 4/1992
(Continued)

OTHER PUBLICATIONS

Office Actions and Responses for related U.S. Appl. No. 11/864,835, filed Sep. 28, 2007; First named Inventor: Celso J. Bagaoisan; dated Mar. 1, 2010-Feb. 4, 2011; 46 pages.
(Continued)

*Primary Examiner* — Dianne Dornbusch
(74) *Attorney, Agent, or Firm* — Arentfox Schiff LLP

(57) ABSTRACT

An apparatus for sealing a puncture includes a positioning member including a proximal end, a distal end sized for insertion into a puncture, an expandable element on the distal end, and a tension indicator on the proximal end. The tension indicator includes a distal housing portion fixed relative to the proximal end, and a proximal housing portion or handle movable proximally relative to the distal housing portion. The handle is biased towards the distal housing portion such that, when sufficient tensile force is applied between the expandable element and the handle, the handle moves away from the distal housing portion. During use, the distal end is introduced through a puncture into a vessel, the expandable element is expanded, and the positioning member is partially withdrawn until the expanded element contacts a wall of the vessel and the handle separates from the distal housing portion, indicating that sufficient tension is applied.

24 Claims, 14 Drawing Sheets

Related U.S. Application Data continuation-in-part of application No. 13/252,061, filed on Oct. 3, 2011, now Pat. No. 9,364,206, which is a continuation-in-part of application No. 12/098,380, filed on Apr. 4, 2008, now Pat. No. 8,029,533.

(52) U.S. Cl.
CPC ............... *A61B 2017/00619* (2013.01); *A61B 2017/00623* (2013.01); *A61B 2017/00654* (2013.01); *A61B 2017/00898* (2013.01)

(58) Field of Classification Search
CPC ........... A61B 2017/00619; A61B 2017/00601; A61B 2017/00557
See application file for complete search history.

(56) References Cited

U.S. PATENT DOCUMENTS

| | | | |
|---|---|---|---|
| 3,765,419 A | 10/1973 | Usher | |
| 4,002,173 A | 1/1977 | Manning et al. | |
| 4,260,077 A | 4/1981 | Schroeder | |
| 4,327,709 A | 5/1982 | Hanson et al. | |
| 4,362,150 A | 12/1982 | Lombardi et al. | |
| 4,472,542 A | 9/1984 | Nambu | |
| 4,540,404 A | 9/1985 | Wolvek | |
| 4,655,211 A | 4/1987 | Sakamoto et al. | |
| 4,664,857 A | 5/1987 | Nambu | |
| 4,734,097 A | 3/1988 | Tanabe et al. | |
| 4,738,658 A | 4/1988 | Magro et al. | |
| 4,801,434 A | 1/1989 | Kido et al. | |
| 4,838,280 A | 6/1989 | Haaga | |
| 4,838,864 A | 6/1989 | Peterson | |
| 4,852,568 A | 8/1989 | Kensey | |
| 4,890,612 A | 1/1990 | Kensey | |
| 5,053,046 A | 10/1991 | Janese | |
| 5,061,274 A | 10/1991 | Kensey | |
| 5,087,246 A | 2/1992 | Smith | |
| 5,104,375 A | 4/1992 | Wolf et al. | |
| 5,104,389 A | 4/1992 | Deem et al. | |
| 5,108,421 A | 4/1992 | Fowler | |
| 5,192,300 A | 3/1993 | Fowler | |
| 5,192,302 A | 3/1993 | Kensey et al. | |
| 5,221,259 A | 6/1993 | Weldon et al. | |
| 5,222,974 A | 6/1993 | Kensey et al. | |
| 5,258,042 A | 11/1993 | Mehta | |
| 5,259,835 A | 11/1993 | Clark et al. | |
| 5,275,616 A | 1/1994 | Fowler | |
| 5,282,827 A | 2/1994 | Kensey et al. | |
| 5,290,310 A | 3/1994 | Makower et al. | |
| 5,292,332 A | 3/1994 | Lee | |
| 5,306,254 A | 4/1994 | Nash et al. | |
| 5,320,639 A | 6/1994 | Rudnick | |
| 5,324,306 A | 6/1994 | Makower et al. | |
| 5,334,216 A | 8/1994 | Vidal et al. | |
| 5,370,660 A | 12/1994 | Weinstein et al. | |
| 5,383,896 A | 1/1995 | Gershony et al. | |
| RE34,866 E | 2/1995 | Kensey et al. | |
| 5,391,183 A | 2/1995 | Janzen et al. | |
| 5,409,703 A | 4/1995 | McAnalley et al. | |
| 5,413,571 A | 5/1995 | Katsaros et al. | |
| 5,419,765 A | 5/1995 | Weldon et al. | |
| 5,431,639 A | 7/1995 | Shaw | |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,464,396 A | 11/1995 | Barta et al. | |
| 5,486,195 A | 1/1996 | Myers et al. | |
| 5,489,278 A | 2/1996 | Abrahamson | |
| 5,514,158 A | 5/1996 | Kanesaka | |
| 5,529,577 A | 6/1996 | Hammerslag | |
| 5,550,187 A | 8/1996 | Woonza et al. | |
| 5,571,181 A | 11/1996 | Li | |
| 5,580,923 A | 12/1996 | Yeung et al. | |
| 5,584,815 A | 12/1996 | Pawelka et al. | |
| 5,591,204 A | 1/1997 | Janzen et al. | |
| 5,591,205 A | 1/1997 | Fowler | |
| 5,601,602 A | 2/1997 | Fowler | |
| 5,626,601 A | 5/1997 | Gershony et al. | |
| 5,637,086 A | 6/1997 | Ferguson et al. | |
| 5,643,464 A | 7/1997 | Rhee et al. | |
| 5,649,959 A | 7/1997 | Hannam et al. | |
| 5,660,849 A | 8/1997 | Polson et al. | |
| 5,681,279 A | 10/1997 | Roper et al. | |
| 5,700,477 A | 12/1997 | Rosenthal et al. | |
| 5,707,393 A | 1/1998 | Kensey et al. | |
| 5,716,375 A | 2/1998 | Fowler | |
| 5,718,916 A | 2/1998 | Scherr | |
| 5,725,498 A | 3/1998 | Janzen et al. | |
| 5,725,551 A | 3/1998 | Myers et al. | |
| 5,728,122 A | 3/1998 | Leschinsky et al. | |
| 5,728,132 A | 3/1998 | Tassel et al. | |
| 5,731,368 A | 3/1998 | Stanley et al. | |
| 5,741,223 A | 4/1998 | Janzen et al. | |
| 5,744,153 A | 4/1998 | Yewey et al. | |
| 5,752,974 A | 5/1998 | Rhee et al. | |
| 5,759,193 A | 6/1998 | Burbank et al. | |
| 5,780,044 A | 7/1998 | Yewey et al. | |
| 5,782,860 A | 7/1998 | Epstein et al. | |
| 5,785,679 A | 7/1998 | Abolfathi et al. | |
| 5,795,331 A | 8/1998 | Cragg et al. | |
| 5,814,016 A | 9/1998 | Valley et al. | |
| 5,830,130 A | 11/1998 | Janzen et al. | |
| 5,836,970 A | 11/1998 | Pandit | |
| 5,843,124 A | 12/1998 | Hammerslag | |
| 5,868,778 A | 2/1999 | Gershony et al. | |
| 5,916,236 A | 6/1999 | Moer et al. | |
| 5,922,009 A | 7/1999 | Epstein et al. | |
| 5,928,266 A | 7/1999 | Kontos | |
| 5,941,847 A | 8/1999 | Huber et al. | |
| 5,948,429 A | 9/1999 | Bell et al. | |
| 5,948,829 A | 9/1999 | Wallajapet et al. | |
| 5,951,583 A | 9/1999 | Jensen et al. | |
| 5,951,589 A * | 9/1999 | Epstein ............ | A61B 17/00491 606/213 |
| 5,957,952 A | 9/1999 | Gershony et al. | |
| 5,972,375 A | 10/1999 | Truter et al. | |
| 5,973,014 A | 10/1999 | Funk et al. | |
| 6,007,563 A | 12/1999 | Nash et al. | |
| 6,017,359 A | 1/2000 | Gershony et al. | |
| 6,022,361 A | 2/2000 | Epstein et al. | |
| 6,027,471 A | 2/2000 | Fallon et al. | |
| 6,045,570 A | 4/2000 | Epstein et al. | |
| 6,048,358 A | 4/2000 | Barak | |
| 6,051,248 A | 4/2000 | Sawhney et al. | |
| 6,056,768 A | 5/2000 | Cates et al. | |
| 6,056,769 A | 5/2000 | Epstein et al. | |
| 6,063,061 A | 5/2000 | Wallace et al. | |
| 6,063,085 A | 5/2000 | Tay et al. | |
| 6,083,522 A | 7/2000 | Chu et al. | |
| 6,086,607 A | 7/2000 | Cragg et al. | |
| 6,090,130 A | 7/2000 | Nash et al. | |
| 6,113,611 A | 9/2000 | Allen et al. | |
| 6,117,145 A | 9/2000 | Wood et al. | |
| 6,152,943 A | 11/2000 | Sawhney | |
| 6,162,192 A | 12/2000 | Cragg et al. | |
| 6,162,240 A | 12/2000 | Cates et al. | |
| 6,162,241 A | 12/2000 | Coury et al. | |
| 6,165,201 A | 12/2000 | Sawhney et al. | |
| 6,179,862 B1 | 1/2001 | Sawhney | |
| 6,179,863 B1 | 1/2001 | Kensey et al. | |
| 6,223,936 B1 | 5/2001 | Jeanbourquin | |
| 6,238,412 B1 | 5/2001 | Dubrul et al. | |
| 6,271,278 B1 | 8/2001 | Park et al. | |
| 6,287,323 B1 | 9/2001 | Hammerslag | |
| 6,296,658 B1 | 10/2001 | Gershony et al. | |
| 6,299,597 B1 | 10/2001 | Buscemi et al. | |
| 6,302,898 B1 | 10/2001 | Edwards et al. | |
| 6,315,753 B1 | 11/2001 | Cragg et al. | |
| 6,325,789 B1 | 12/2001 | Janzen et al. | |
| 6,350,274 B1 | 2/2002 | Li | |
| 6,368,300 B1 | 4/2002 | Fallon et al. | |
| 6,371,975 B2 | 4/2002 | Cruise et al. | |

(56) References Cited

U.S. PATENT DOCUMENTS

| | | |
|---|---|---|
| 6,379,373 B1 | 4/2002 | Sawhney et al. |
| 6,458,147 B1 | 10/2002 | Cruise et al. |
| 6,464,712 B1 | 10/2002 | Epstein et al. |
| 6,475,177 B1 | 11/2002 | Suzuki |
| 6,514,534 B1 | 2/2003 | Sawhney |
| 6,540,735 B1 | 4/2003 | Ashby et al. |
| 6,562,059 B2 | 5/2003 | Edwards et al. |
| 6,566,406 B1 | 5/2003 | Pathak et al. |
| 6,569,185 B2 | 5/2003 | Ungs |
| 6,605,294 B2 | 8/2003 | Sawhney |
| 6,608,117 B1 | 8/2003 | Gvozdic |
| 6,610,026 B2 | 8/2003 | Cragg et al. |
| 6,613,070 B2 | 9/2003 | Redmond et al. |
| 6,626,861 B1 | 9/2003 | Hart et al. |
| 6,626,918 B1 | 9/2003 | Ginn et al. |
| 6,635,068 B1 | 10/2003 | Dubrul et al. |
| 6,689,148 B2 | 2/2004 | Sawhney et al. |
| 6,699,261 B1 | 3/2004 | Cates et al. |
| 6,703,047 B2 | 3/2004 | Sawhney et al. |
| 6,774,151 B2 | 8/2004 | Malmgren et al. |
| 6,818,008 B1 | 11/2004 | Cates et al. |
| 6,818,018 B1 | 11/2004 | Sawhney |
| 6,860,895 B1 | 3/2005 | Akerfeldt et al. |
| 6,863,924 B2 | 3/2005 | Ranganathan et al. |
| 6,887,974 B2 | 5/2005 | Pathak |
| 6,890,342 B2 | 5/2005 | Zhu et al. |
| 6,890,343 B2 | 5/2005 | Ginn et al. |
| 6,960,617 B2 | 11/2005 | Omidian et al. |
| 6,994,686 B2 | 2/2006 | Cruise et al. |
| 7,009,034 B2 | 3/2006 | Pathak et al. |
| 7,118,578 B2 | 10/2006 | West et al. |
| 7,316,704 B2 | 1/2008 | Bagaoisan et al. |
| 7,331,979 B2 | 2/2008 | Khosravi et al. |
| 7,335,220 B2 | 2/2008 | Khosravi et al. |
| 7,553,319 B2 | 6/2009 | Bagaoisan et al. |
| 7,572,274 B2 | 8/2009 | Yassinzadeh |
| 7,611,479 B2 | 11/2009 | Cragg et al. |
| 7,618,438 B2 | 11/2009 | White et al. |
| 7,621,936 B2 | 11/2009 | Cragg et al. |
| 7,662,161 B2 | 2/2010 | Briganti et al. |
| 7,790,192 B2 | 9/2010 | Sawhney et al. |
| 7,806,856 B2 | 10/2010 | Bagaoisan et al. |
| 7,850,710 B2 | 12/2010 | Huss |
| 7,955,353 B1 | 6/2011 | Ashby et al. |
| 3,002,742 A1 | 8/2011 | Pai et al. |
| 7,988,706 B2 | 8/2011 | Forsberg et al. |
| 7,993,367 B2 | 8/2011 | Bagaoisan et al. |
| 8,029,533 B2 | 10/2011 | Bagaoisan et al. |
| 8,262,693 B2 | 9/2012 | Pai et al. |
| 8,568,445 B2 | 10/2013 | Pipenhagen et al. |
| 8,795,709 B2 | 8/2014 | Sawhney et al. |
| 8,870,917 B2 | 10/2014 | Walters |
| 9,289,195 B2 | 3/2016 | Bagaoisan et al. |
| 9,364,206 B2 | 6/2016 | Bagaoisan et al. |
| 9,668,719 B2 | 6/2017 | Tegels et al. |
| 9,895,144 B2 | 2/2018 | Tegels et al. |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0015724 A1 | 2/2002 | Yang et al. |
| 2002/0062104 A1 | 5/2002 | Ashby et al. |
| 2002/0072767 A1 | 6/2002 | Zhu |
| 2002/0106409 A1 | 8/2002 | Sawhney et al. |
| 2002/0111392 A1 | 8/2002 | Cruise |
| 2002/0111651 A1 | 8/2002 | Ungs |
| 2002/0120228 A1 | 8/2002 | Maa et al. |
| 2002/0188319 A1 | 12/2002 | Morris et al. |
| 2002/0193808 A1 | 12/2002 | Belef et al. |
| 2003/0008831 A1 | 1/2003 | Yang et al. |
| 2003/0012734 A1 | 1/2003 | Pathak et al. |
| 2003/0051735 A1 | 3/2003 | Pavcnik et al. |
| 2003/0061735 A1 | 4/2003 | Polifroni |
| 2003/0088269 A1 | 5/2003 | Ashby |
| 2003/0088271 A1 | 5/2003 | Cragg et al. |
| 2003/0109899 A1 | 6/2003 | Fisher et al. |
| 2003/0135234 A1 | 7/2003 | Fisher et al. |
| 2003/0135235 A1 | 7/2003 | Fisher et al. |
| 2003/0135236 A1 | 7/2003 | Fisher et al. |
| 2003/0135237 A1 | 7/2003 | Cragg et al. |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0139773 A1 | 7/2003 | Fisher et al. |
| 2003/0233120 A1 | 12/2003 | Akerfeldt et al. |
| 2004/0010287 A1 | 1/2004 | Bonutti |
| 2004/0122350 A1 | 6/2004 | Zhong et al. |
| 2004/0143290 A1 | 7/2004 | Brightbill |
| 2004/0147016 A1 | 7/2004 | Rowley et al. |
| 2004/0176798 A1 | 9/2004 | Epstein et al. |
| 2004/0236262 A1 | 11/2004 | McIntosh et al. |
| 2004/0249342 A1 | 12/2004 | Khosravi et al. |
| 2004/0267193 A1 | 12/2004 | Bagaoisan et al. |
| 2004/0267307 A1 | 12/2004 | Bagaoisan et al. |
| 2004/0267308 A1 | 12/2004 | Bagaoisan et al. |
| 2005/0085773 A1 | 4/2005 | Forsberg et al. |
| 2005/0085851 A1 | 4/2005 | Fiehler et al. |
| 2005/0085852 A1 | 4/2005 | Ditter |
| 2005/0085855 A1 | 4/2005 | Forsberg et al. |
| 2005/0267522 A1* | 12/2005 | Yassinzadeh ...... A61B 17/0057 606/213 |
| 2005/0277980 A1 | 12/2005 | Yassinzadeh |
| 2006/0034930 A1 | 2/2006 | Sawhney et al. |
| 2006/0099238 A1 | 5/2006 | Khosravi et al. |
| 2006/0100664 A1 | 5/2006 | Pai et al. |
| 2006/0161188 A1 | 7/2006 | Kennedy et al. |
| 2006/0229673 A1 | 10/2006 | Forsberg et al. |
| 2006/0229674 A1 | 10/2006 | Forsberg et al. |
| 2006/0241579 A1 | 10/2006 | Kawaura et al. |
| 2006/0253037 A1 | 11/2006 | Ginn et al. |
| 2006/0253072 A1 | 11/2006 | Pai et al. |
| 2006/0265007 A1 | 11/2006 | White et al. |
| 2007/0060950 A1 | 3/2007 | Khosravi et al. |
| 2007/0088362 A1 | 4/2007 | Bonutti et al. |
| 2007/0231366 A1 | 10/2007 | Sawhney et al. |
| 2007/0255314 A1 | 11/2007 | Forsberg et al. |
| 2008/0009794 A1 | 1/2008 | Bagaoisan et al. |
| 2008/0082122 A1 | 4/2008 | Khosravi et al. |
| 2008/0221615 A1 | 9/2008 | Ginn et al. |
| 2008/0243182 A1 | 10/2008 | Bates et al. |
| 2008/0269800 A1 | 10/2008 | Spurchise et al. |
| 2009/0088793 A1 | 4/2009 | Bagaoisan et al. |
| 2009/0318955 A1 | 12/2009 | Dave et al. |
| 2010/0211000 A1 | 8/2010 | Killion et al. |
| 2013/0190813 A1 | 7/2013 | Tegels et al. |
| 2014/0135826 A1 | 5/2014 | Tegels et al. |
| 2014/0180334 A1 | 6/2014 | Bagaoisan et al. |
| 2016/0324511 A1 | 11/2016 | Bagaoisan et al. |

FOREIGN PATENT DOCUMENTS

| | | |
|---|---|---|
| EP | 0716833 A2 | 6/1996 |
| EP | 2811912 B1 | 6/2017 |
| WO | 9222252 A1 | 12/1992 |
| WO | 9413210 A1 | 6/1994 |
| WO | 9428798 A1 | 12/1994 |
| WO | 9922646 A1 | 5/1999 |
| WO | 0014155 A1 | 3/2000 |
| WO | 0019912 A1 | 4/2000 |
| WO | 03004749 A1 | 1/2003 |
| WO | 03009764 A1 | 2/2003 |
| WO | 03087254 A2 | 10/2003 |
| WO | 03094749 A1 | 11/2003 |
| WO | 2006115904 A2 | 11/2006 |
| WO | 2008036634 A1 | 3/2008 |

OTHER PUBLICATIONS

Office Actions and Responses for related U.S. Appl. No. 12/098,380, correspondence dated Sep. 23, 2010-Jun. 14, 2011; 48 pages.
PCT International Search Report and Written Opinion for PCT/US2008/077406, Applicant: AccessClosure, Inc., Forms PCT/ISA/

(56) References Cited

OTHER PUBLICATIONS

220, PCT/ISA/210, and PCT/ISA/237; dated Dec. 22, 2008, 11 pages.
St. Jude Medical, Angio-Seal Evolution Vascular Closure Device, Instructions for Use, 2008, 12 pages.

* cited by examiner

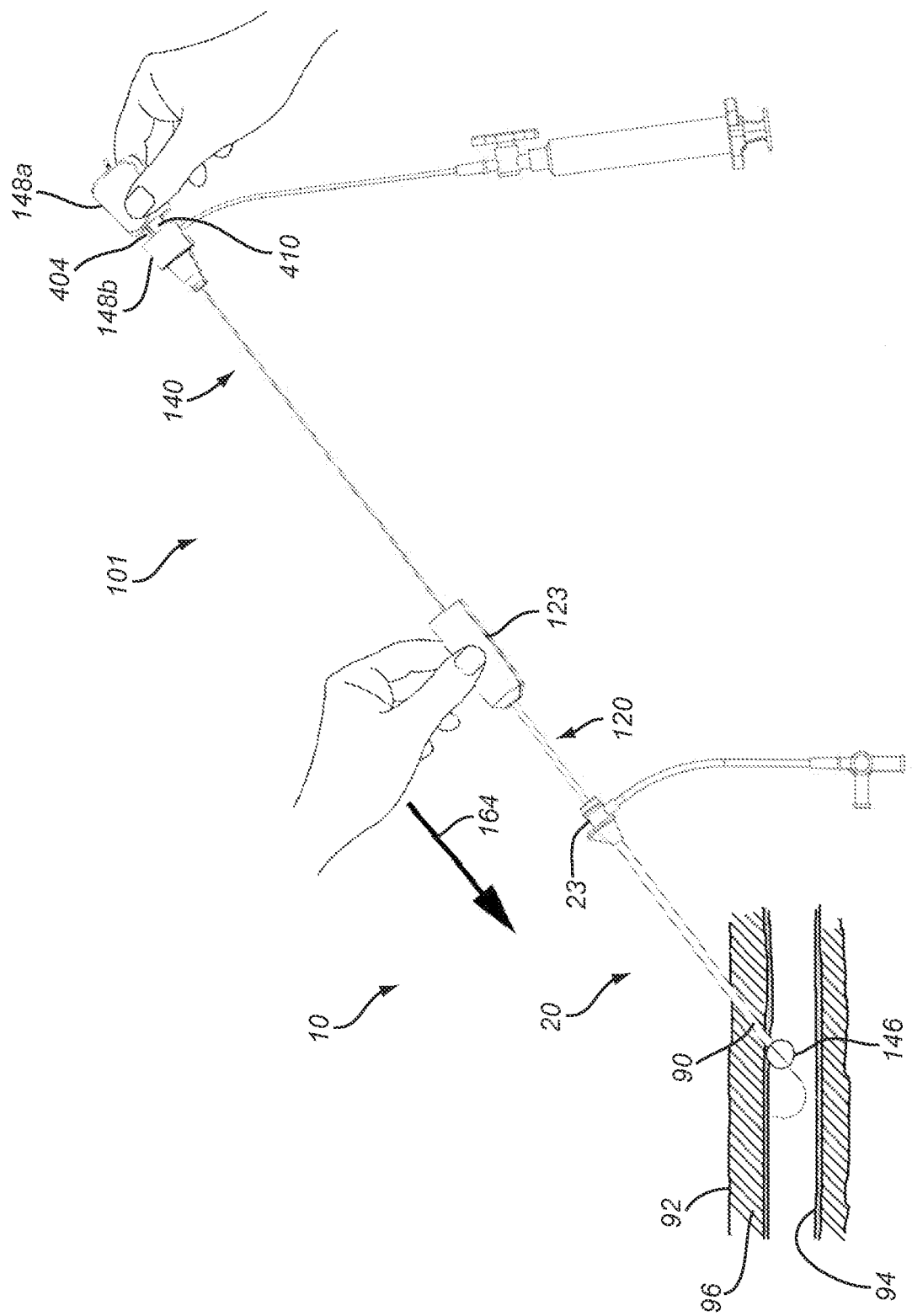

APPARATUS AND METHODS FOR SEALING A VASCULAR PUNCTURE

CROSS-REFERENCE TO RELATED APPLICATIONS

This application is a divisional of U.S. patent application Ser. No. 14/191,237, filed on Feb. 26, 2014, titled "APPARATUS AND METHODS FOR SEALING A VASCULAR PUNCTURE", which is a continuation-in-part of U.S. patent application Ser. No. 13/252,061, filed on Oct. 3, 2011, titled "APPARATUS AND METHODS FOR SEALING A VASCULAR PUNCTURE", which is a continuation-in-part of U.S. patent application Ser. No. 12/098,380, filed on Apr. 4, 2008, titled "APPARATUS AND METHODS FOR SEALING A VASCULAR PUNCTURE", all of which are incorporated herein by reference in their entirety.

FIELD OF THE INVENTION

The present invention relates generally to apparatus and methods for sealing punctures in a body, and more particularly, to apparatus and methods for sealing a vascular puncture extending through tissue into a blood vessel, and to apparatus and methods for delivering a plug, sealant, and/or other material into a percutaneous puncture extending from a patient's skin to a blood vessel or other body lumen, e.g., to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

SUMMARY OF THE INVENTION

The present invention is directed to apparatus and methods for sealing a puncture in a body, and, more particularly, to apparatus and methods for providing temporary or permanent hemostasis within a vascular puncture extending into a blood vessel, and/or to apparatus and methods for delivering a sealant and/or other material into a percutaneous puncture extending from a patient's skin to a blood vessel or other body lumen.

In accordance with one embodiment, a system is provided for sealing a puncture extending through tissue that includes an introducer sheath and an elongate positioning or occlusion member. The introducer sheath includes a lumen and a distal end sized for insertion through a puncture. The elongate positioning member is sized for insertion into the introducer sheath lumen and includes an expandable element on a distal end of the positioning member and a tension indicator on a proximal end of the positioning member. Optionally, the system may include a sealant cartridge including a tubular member, a sealant disposed within the tubular member and a pusher member disposed within the tubular member for deploying the sealant distally from the tubular member when the tubular member is retracted proximally relative to the pusher member.

The tension indicator on the proximal end of the positioning member includes a proximal housing portion, a distal housing portion and a spring coupled to the proximal housing portion and the distal housing portion. The spring biases the proximal and distal housing portions together in a first position yet allows the proximal and distal housing portions to separate to a second extended position, e.g., where the spring is compressed or otherwise directed to a higher potential energy state. For example, a force sufficient to overcome the spring's bias may be less than a desired tension force applied to the positioning member during use, e.g., when the positioning member is pulled to cause the expandable element in an expanded position to contact a wall of a vessel sufficiently to seal the vessel from the puncture and/or avoid tenting of the wall of the vessel.

In one embodiment, the spring of the tension indicator may extend between a spring retaining ring and a shoulder portion of the proximal housing portion. Further, the spring may be disposed around a hollow cylinder and the hollow cylinder may be coupled to the distal housing portion. The hollow cylinder may be disposed around an internal cylindrical element and the internal cylindrical element and the hollow cylinder may be coupled to the spring retaining ring.

In accordance with another embodiment, an apparatus is provided for providing temporary hemostasis within a puncture extending through tissue to a body lumen. The tension indicator apparatus includes an elongate member with a proximal end, a distal end sized for introduction into a puncture through tissue, an expandable element on the distal end, and a tension indicator on the proximal end. In a collapsed condition, the expandable element is sized for introduction through the puncture into the body lumen and, in an expanded condition, the expandable element is larger than the puncture such that the expandable element may be pulled against a wall of the body lumen adjacent the puncture. The tension indicator is configured to indicate when sufficient is applied to the wall when the elongate member is pulled.

In one embodiment, the tension indicator includes a proximal housing portion configured to be held by a user, and a distal housing portion, the proximal and distal housing portions being movable away from one another, yet biased to move towards or against one another. For example, a spring, e.g., a compression or extension spring, may be disposed within the proximal housing portion for biasing the proximal housing portion towards the distal housing portion. When the spring bias is overcome, the proximal housing portion may move proximally away from the distal housing portion, thereby creating a space between the proximal and distal housing portions. The space may serve as a visual cue that the optimum amount of tension is being applied by the elongate member. The spring may have a spring constant selected such that a tension force sufficient to overcome the bias of the spring and cause the proximal housing portion to separate from the distal housing portion may correspond to the optimum amount of tension to be applied to provide temporary hemostasis without tenting the vessel wall or pulling the temporary hemostasis element out of the puncture tract during use. Thus, the spring constant may be selected to apply sufficient force against the wall of the body lumen by expandable element to substantially seal the body lumen from the puncture.

In accordance with still another embodiment, a method is provided for sealing a puncture extending through tissue to a body lumen. The method includes introducing an elongate member into the puncture until an expandable element thereon is disposed within the body lumen, expanding the expandable element within the body lumen, and retracting the elongate member until the expanded expandable element contacts a wall of the body lumen adjacent the puncture and a tension indicator on the elongate member indicates that sufficient tension is applied to the wall of the body lumen by the expandable element to substantially seal the puncture. Retracting the elongate member may include separating a proximal housing portion of the tension indicator from a distal housing portion of the tension indicator when the desired amount of tension is applied. In one embodiment, the tension indicator includes a spring and separating the proximal housing portion from the distal housing portion may include compressing the spring.

Optionally, the method may include one or more additional steps. For example, an introducer sheath may be introduced into the puncture before introducing the elongate member, and the elongate member may be introduced into the puncture through the introducer sheath. In addition or alternatively, a tubular member or other cartridge carrying a sealant therein may be advanced along the elongate member and into the puncture, and then retracted to expose the sealant within the puncture. After use, the expandable element may be collapsed, and the elongate member removed from the puncture, e.g., through any sealant delivered into the puncture.

Other aspects and features of the present invention will become apparent from consideration of the following description taken in conjunction with the accompanying drawings.

BRIEF DESCRIPTION OF THE DRAWINGS

FIGS. 6A, 7A, 8A, 9A, and 10A are partial cross-sectional side views of a patient's body illustrating a method of using the system of FIG. 1B for sealing a puncture.

DETAILED DESCRIPTION OF THE EXEMPLARY EMBODIMENTS

Figure 1A:
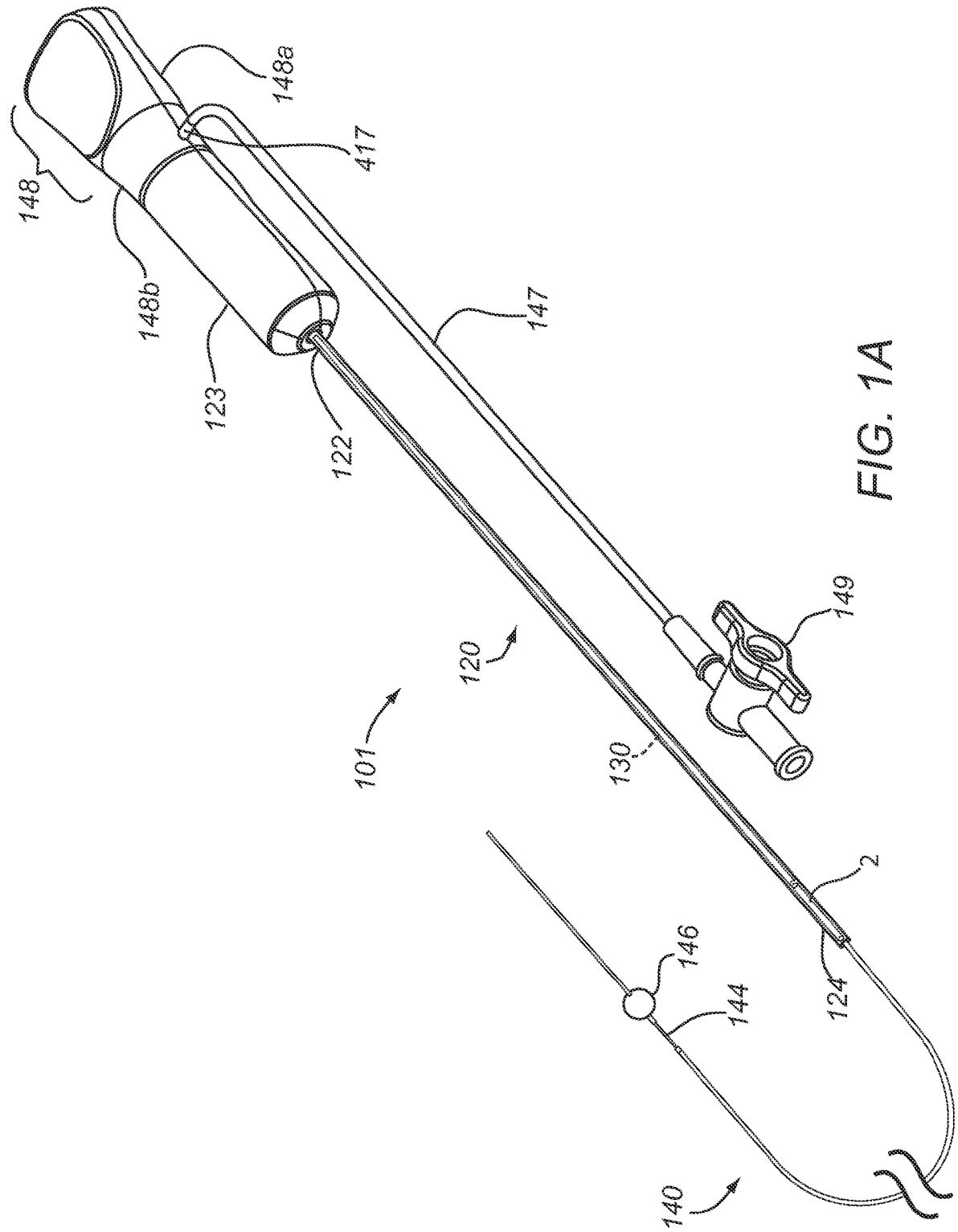
FIG. 1A is a perspective view of an exemplary embodiment of an apparatus for delivering a sealant into a puncture through tissue, including a cartridge carrying the sealant and a positioning member.
Figure 1B:
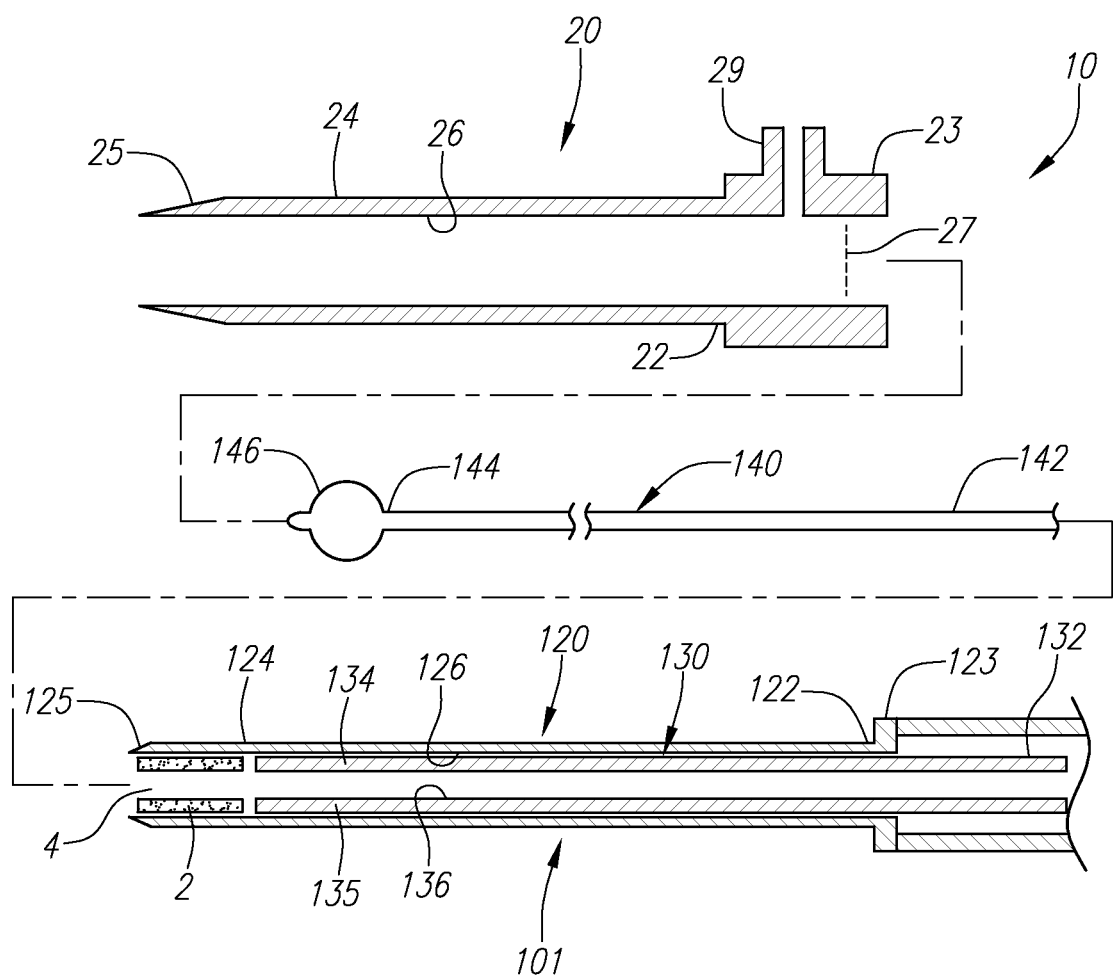
FIG. 1B is an exploded cross-sectional side view of a system for delivering a sealant into a puncture through tissue, including the apparatus of FIG. 1A (only partially shown) and an introducer sheath.

Turning to the drawings, FIGS. 1A and 1B show an exemplary embodiment of an apparatus 101 and a system 10, respectively, for sealing a puncture through tissue. Generally, as shown in FIG. 1A, the apparatus 101 includes a cartridge or other tubular member 120, a sealant 2 carried by the cartridge 120, a plunger, tamping member, or other pusher member 130 also carried by the cartridge 120, a cartridge hub 123, a positioning or occlusion member 140, and a positioning member housing 148. As shown in FIG. 1B, the apparatus 101 may be part of a system 10, e.g., which may also include a delivery, access, procedure, introducer, or other sheath 20. Optionally, the system 10 may include one or more other components, e.g., a needle, guidewire, and/or other instrument(s) for creating a puncture (not shown), and/or a source of additional sealing compound (also not shown), e.g., to provide a kit that may be provided to a user.

As best seen in FIG. 1B, the introducer sheath 20 may be a generally tubular body including a proximal end 22, a distal end 24 sized for insertion into a puncture through tissue, and a lumen 26 extending between the proximal and distal ends 22 and 24. The introducer sheath 20 may be formed from a substantially rigid, semi-rigid, and/or flexible tubular body including a hub 23 on the proximal end 22. The introducer sheath 20 may have sufficient length to extend from a patient's skin through any intervening tissue into a blood vessel or other body lumen, e.g., having a length between about ten centimeters and twenty centimeters (10-20 cm), and may have an outer diameter between about 1.6 millimeters and 4 millimeters (1.6-4 mm). The distal end 24 may be tapered and/or may include a substantially atraumatic distal tip 25 for facilitating advancement through a puncture.

The introducer sheath 20 may be formed using known materials and/or methods, e.g., plastic with the tubular body and hub 23 substantially permanently connected together, e.g., using an interference fit, one or more mating connectors (not shown), bonding with adhesive, sonic welding, and the like. The hub 23 generally includes one or more seals (not shown) adjacent an opening 27, which may prevent flow of blood or other fluids out of the hub 23 from the lumen 26, yet accommodate insertion of one or more instruments into the lumen 26, such as the cartridge 120. Optionally, as shown, the hub 23 may include a side port 29 communicating with the lumen 26, e.g., for coupling a source of saline or other fluid (not shown) to the hub 23.

With additional reference to FIG. 1B, the cartridge 120 is generally an elongate tubular body including a proximal end 122, a distal end 124 sized for introduction into the lumen 26 of the introducer sheath 20, and a lumen 126 extending between the proximal and distal ends 122 and 124. The cartridge 120 may be substantially rigid, semi-rigid, or flexible, e.g., such that the cartridge 120 may be advanced through the introducer sheath 20 or otherwise into a puncture through tissue. The cartridge 120 may also include a tapered distal tip 125 and/or an enlarged handle or hub 123 on the proximal end 122.

A sealant 2 is provided in the distal portion of the cartridge 120 and a pusher member 130 is provided proximal to the sealant 2 within the cartridge 120. The sealant 2 may include a biocompatible, bioabsorbable, and/or expandable material, such as a freeze-dried hydrogel. The sealant 2 may have a solid or hollow cylindrical shape, a rolled sheet shape, a disk shape, or other shapes or cross-sections, such as elliptical, triangular, square, conical, disk, or polygonal shapes. For example, the sealant 2 may be formed from a solid material including a lumen 4 extending between proximal and distal ends thereof, as shown in FIG. 1B. The lumen 4 may be created by rolling a sheet of material around a mandrel, by molding, by boring into or otherwise removing material from an already formed solid material, and the like. The lumen 4 may be dimensioned such that the positioning member 140, a guidewire or other instrument (not shown) may slide or otherwise pass through the sealant 2, as described elsewhere herein.

The sealant 2 may be substantially homogeneous or may include one or more different materials at one or more locations. For example, in one embodiment, the sealant 2 may include a carrier or core having first and second hydrogel precursors disposed thereon in an unreactive state, which may provide an adherent coating when the sealant 2 is exposed to an aqueous environment. In one embodiment, the sealant 2 may be formed from a biocompatible and/or bioabsorbable hydrogel, e.g., polyethylene glycol ("PEG"), or other synthetic material. For example, the hydrogel may include a lyophilized (i.e., freeze-dried) PEG polymer that includes hydrolytically degradable chemical groups, e.g., including a macroporous polymer network, which may uptake fluid and expand when exposed to an aqueous environment. The magnitude of expansion or swelling (pre to post hydration) may be significant, e.g., between about two and ten times (2x-10x) its lyophilized size based on volume.

In addition or alternatively, the sealant 2 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. Optionally, the sealant 2 may include one or more therapeutic and/or pharmaceutical agents, e.g., to promote healing, prevent infection, and/or other adverse medical events, and the like. Such agents may be embedded in the sealant material and/or applied as one or more coatings or layers. Exemplary materials and methods for making and using them are disclosed in U.S. Pat. Nos. 6,152,943, 6,165,201, 6,179,862, 6,514,534, 6,379,373, 6,703,047, 7,009,034, 6,887,974, and in co-pending U.S. patent application Ser. No. 10/454,362, filed Jun. 4, 2003, published as US 2004/0249342, Ser. No. 10/982,387, filed Nov. 5, 2004, published as US 2006/0034930, Ser. No. 10/982,384, filed Nov. 5, 2004, published as US 2006/0099238, and Ser. No. 11/465,791, filed Aug. 18, 2006 published as US 2007/0231366. The disclosures of these references are expressly incorporated by reference herein.

The sealant 2 may be disposed within the lumen 126 of the cartridge 120 proximate to the distal end 124, e.g., immediately adjacent the distal tip 125. Thus, when advanced into the introducer sheath 20 or otherwise within the puncture 90, the sealant 2 may remain out of direct or indirect contact with blood or other bodily fluids along the blood path. Optionally, the cartridge 120 may include a split distal end (not shown), e.g., formed by creating one or more relatively short longitudinal cuts or slots extending proximally from the distal end 124. The split distal end may facilitate retraction of the cartridge 120 relative to the sealant 2, e.g., by providing extra flexibility at the distal end 124, which may allow the distal end 124 to separate more easily from the sealant 2, e.g., as the sealant begins to expand upon being exposed to an aqueous environment, such as blood or other bodily fluids. The lumen 126 may be sized such that the cartridge 120 and sealant 2 are slidable relative to one another, e.g., to allow the cartridge 120 to be refracted proximally relative to the sealant 2 and/or pusher member 130.

With further reference to FIG. 1B, the pusher member 130 may be an elongate tubular body, e.g., a plunger or catheter, including a proximal end 132, a distal end 134 sized for introduction into the lumen 126 of the cartridge 120, and a lumen 136 extending between the proximal and distal ends 132, 134. The pusher member 130 may be sized for being slidably received within the lumen 126 of the cartridge 120, although the pusher member 130 may abut or otherwise interact with the hub 123 of the cartridge 120 such that the pusher member 130 is advanced distally when the cartridge 120 is advanced distally. The distal end 134 of the pusher member 130 may terminate in a substantially blunt distal tip 135, e.g., to facilitate contacting, pushing, and/or "cinching" the sealant 2 within a puncture, as described further below.

The pusher member 130 may be substantially rigid, semi-rigid, and/or substantially flexible, having sufficient column strength to allow proximal movement of the cartridge 120 relative to the sealant 2 without buckling the pusher member 130 and/or to allow the distal tip 135 of the pusher member 130 to be "tamped" down on sealant 2 within a puncture, e.g., by pushing from the proximal end 132, as described elsewhere herein. The lumen 136 of the pusher member 130 may be sized to accommodate the positioning member 140, a guidewire (not shown), a flowable sealing compound, and/or fluid therethrough.

Figure 5:
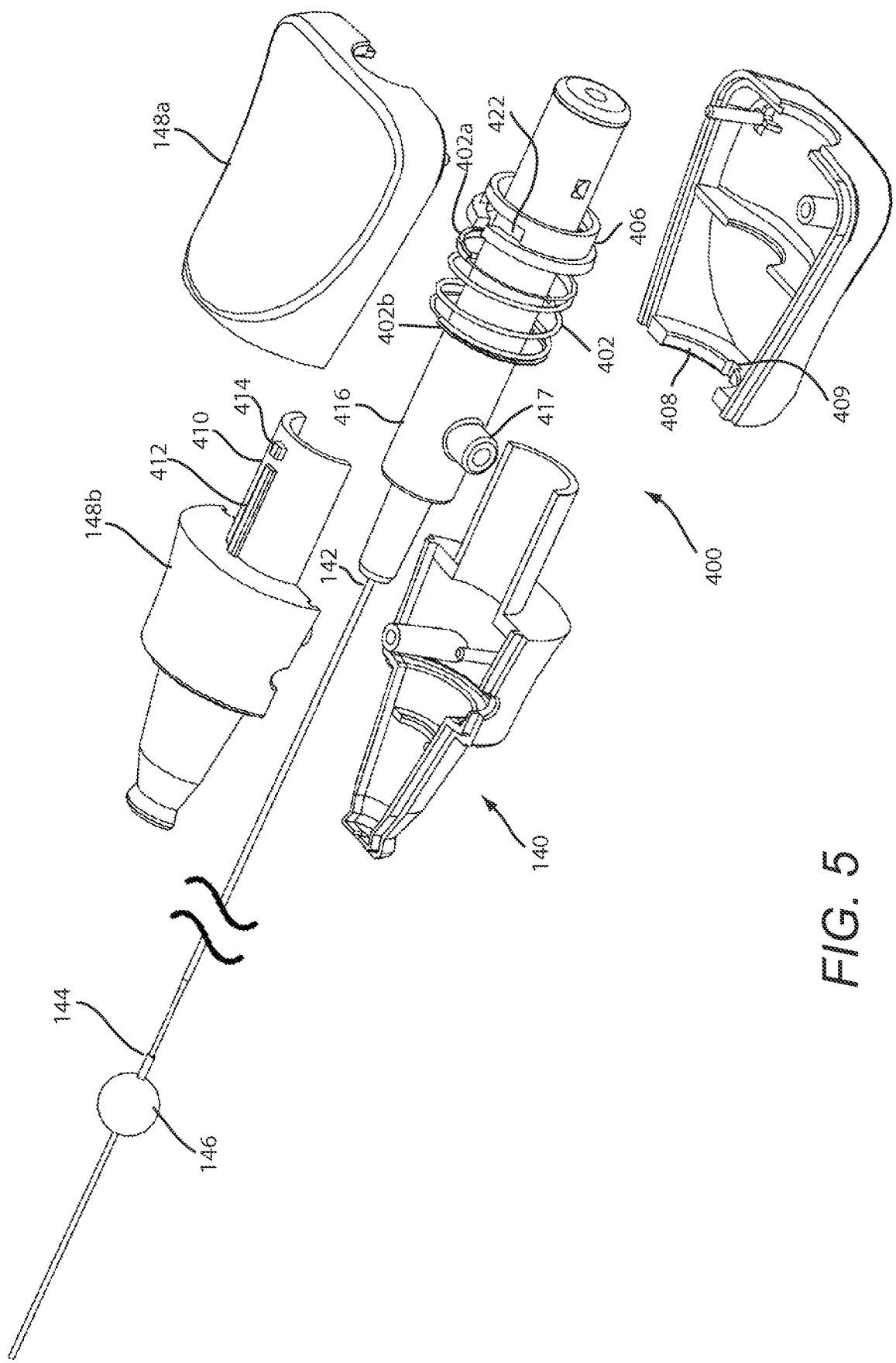
FIG. 5 is an exploded perspective view of the tension indicator assembly of FIGS. 3A-4B.

With continued reference to FIGS. 1A, 1B, and 5, the positioning member 140 generally is an elongate member including a proximal end 142, a distal end 144, a positioning or occlusion element 146 on the distal end 144, and a hollow cylinder or other housing 416 on the proximal end 142. The positioning element 146 may be an expandable member, such as a balloon, a wire mesh structure, an expandable frame, and the like. The positioning element 146 may be selectively expandable, e.g., using a source of inflation media, a pull wire, and/or other actuator (not shown), operable from the proximal end 142 of the positioning member 140.

For example, as shown in FIGS. 1A and 1B, the positioning element may be a balloon 146, and the positioning member 140 may be a tubular body including a lumen (not shown) extending between the proximal and distal ends 142, 144 and communicating with an interior of the balloon 146. In this embodiment, the cylinder 416 may include an inner chamber communicating with the lumen and a source of inflation media. For example, a syringe (not shown) may be coupled to stop cock 149 such that, when the stop cock 149 is opened, the interior of the syringe may communicate with the chamber (and consequently the lumen and interior of the balloon 146) via tubing 147 connected to a port 417 on the cylinder 416. Optionally, the positioning member 140 may include an internal pull wire and piston arrangement (not shown) that causes the balloon 146 to shorten during expansion and extend during collapse. Exemplary embodiments of positioning members 140 including balloons that may be used are disclosed in co-pending U.S. patent application Ser. No. 10/454,362, filed Jun. 4, 2003, published as US 2004/0249342, Ser. No. 11/112,877, filed Apr. 22, 2005, published as US 2006/0253072, and Ser. No. 11/112,971, filed Apr. 22, 2005, and published as US 2008/0009794. The entire disclosures of these references are expressly incorporated by reference herein.

Alternatively, the positioning element may be biased to an enlarged condition, but may be compressed to a contracted condition, e.g., by an overlying sleeve or other constraint (not shown). The constraint may be removed to expose the positioning element, allowing the expandable element to automatically expand to the enlarged condition. Additional information on expandable structures that may be provided on the positioning member 140 may be found in U.S. Pat. Nos. 6,238,412, 6,635,068, and 6,890,343. The entire disclosures of these references are expressly incorporated herein by reference.

Figure 2A:
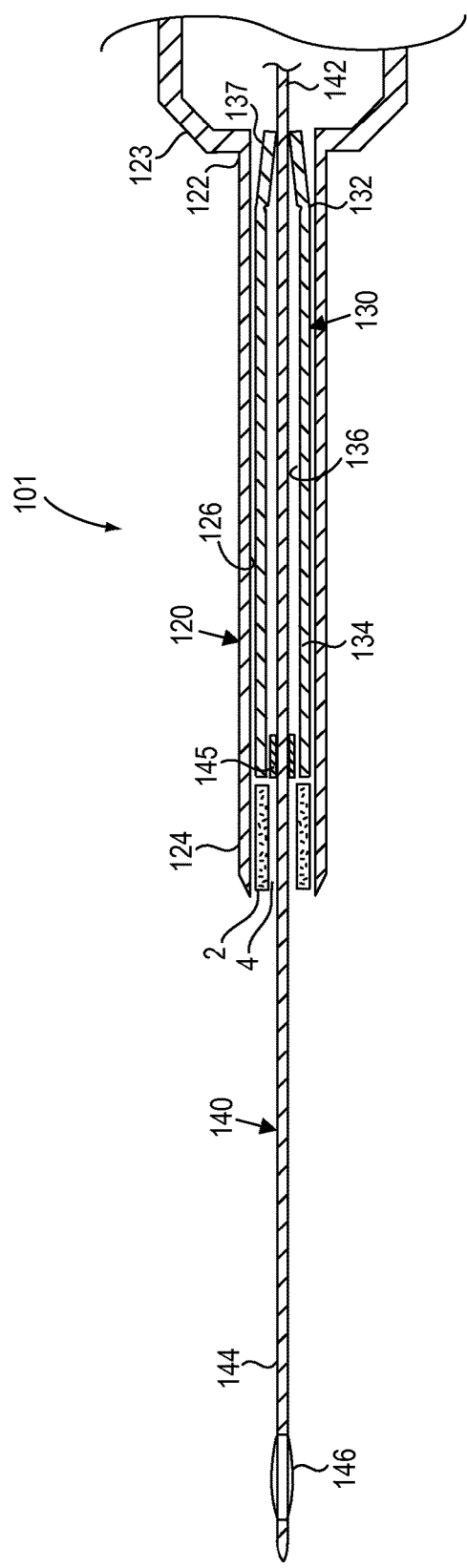
FIGS. 2A and 2B are cross-sectional views of the apparatus of FIGS. 1A and 1B, with the cartridge in proximal and distal positions, respectively.
Figure 2B:
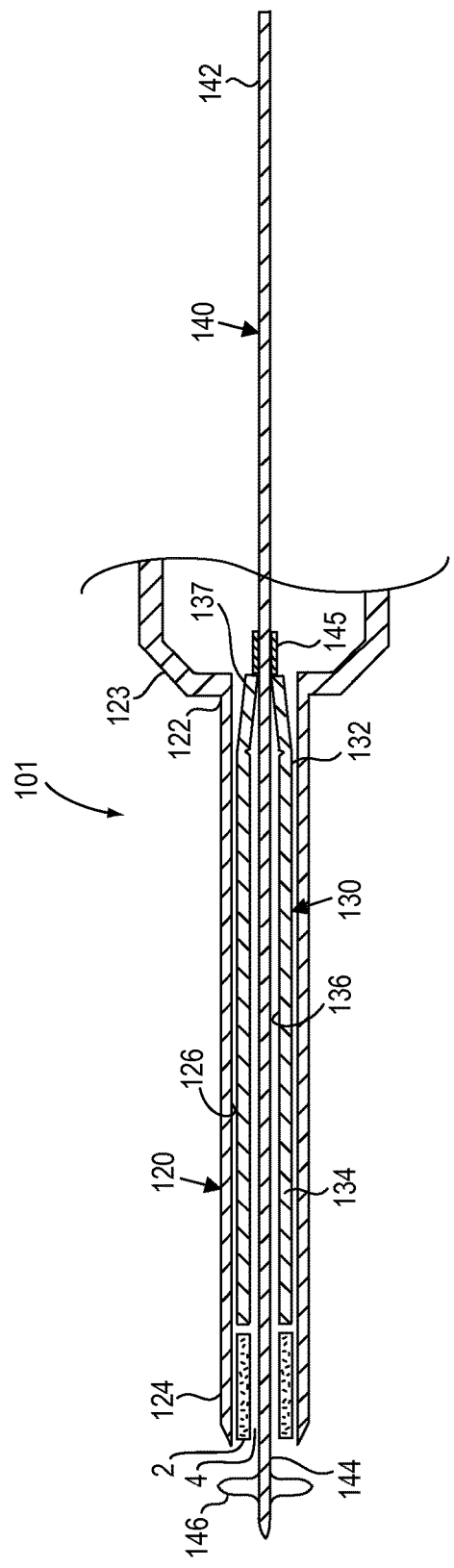

Turning to FIGS. 2A and 2B, the apparatus 101 may be used to position and deliver the sealant 2 within a puncture, e.g., extra-vascularly just above or otherwise adjacent to an arteriotomy in a blood vessel or other body lumen communicating with a puncture, as described further elsewhere herein. In one embodiment, as shown in FIG. 2A, the cartridge 120 (along with the pusher member 130 and sealant 2) may be initially provided on the proximal end 142 of the positioning member 140. For example, the housing 148 (not shown in FIGS. 2A and 2B, see FIG. 1A) on the positioning member 140 and the hub 123 on the cartridge 120 may initially be connected to one another, e.g., using one or more releasable detents (not shown) and the like. The cartridge 120 may be slidable distally along the positioning member 140, e.g., by disconnecting the hub 123 from the housing 148, and then advancing the cartridge 120 until the distal end 124 of the cartridge 120 is disposed adjacent the positioning element 146, as shown in FIG. 2B. For example, the detents may simply separate from one another when the hub 123 is advanced away from the housing 148 with sufficient force. Alternatively, one of the hub 123 and housing 148 may include an actuator or lock (not shown) that may be activated to separate the detents and/or otherwise allow the cartridge 120 to be advanced relative to the positioning member 140. Alternatively, the cartridge member 120 and pusher member 130 may be initially provided adjacent the distal end 144 of the positioning member 140, as shown in FIG. 2B.

Optionally, the positioning member 140 and/or pusher member 130 may include one or more elements that engage when the cartridge 120 reaches a predetermined location when advanced distally along the positioning member 140, e.g., to limit subsequent proximal movement of the pusher member 130 relative to the positioning member 140. For example, as shown in FIGS. 2A and 2B, the positioning member 140 may include a ring, tab, or other raised element 145 at a predetermined location and the pusher member 130 may include a living hinge, tab, or other latch element 137 on the proximal end 132. For example, the latch element 137 may simply be an annular notch in the proximal end 132 of the pusher member 130 to bias the proximal end inwardly.

As an alternative to the latch element(s) 137, the pusher member 130 may simply include a relatively narrow region on the proximal end 132. Further alternatively, the latch element(s) 137 may be replaced by a separate collar or sleeve, one or more inwardly oriented detents, and the like (not shown) attached to or otherwise formed on the proximal end 132 of the pusher member 130. As an alternative to the raised element 145, the positioning member 140 may include a reduced diameter region (not shown) formed by providing a larger tube around a smaller inner tube or by machining, etching, or otherwise removing a portion of the tubular body of the positioning member 140 distal to the reduced region and the pusher member 130 may include a corresponding element (also not shown) that may allow distal advancement but prevent proximal retraction once the pusher member 130 is advanced a predetermined distance. Exemplary embodiments of cooperating elements are disclosed in co-pending U.S. patent application Ser. No. 10/982,384, filed Nov. 5, 2004, published as US 2006/0099238 and [Ser. No. 11/864,835, filed Sep. 28, 2007. The entire disclosures of these references are expressly incorporated by reference herein.

The reduced region (not shown) or raised element 145 may be provided at a predetermined location on the positioning member 140, e.g., a predetermined distance from the positioning element 146 that corresponds to a length of the pusher member 130. As the cartridge 120 (and consequently the pusher member 130) is advanced over the positioning member 140, e.g., until the sealant 2 is disposed adjacent the positioning element 146, the latch element 137 may pass freely over the raised element 145. Thereafter, the latch element 137 may prevent the pusher member 130 from being retracted again past the raised element 145 due to the blunt edge of the latch element 137 abutting the raised element 145.

Alternatively, the pusher member 130 may be fixed relative to the positioning member 140, for example, mechanically bonded, chemically bonded, interference fit, and the like. For example, the distal end 134 of the pusher member 130 may be fixed a predetermined distance proximal to the positioning element 146, e.g., to provide the sealant 2 immediately adjacent the positioning element 146, as shown in FIG. 2B. Additional information on such alternatives and methods for making and using them may be found in co-pending U.S. patent application Ser. No. 11/854,534, filed Sep. 12, 2007, the entire disclosure of which is expressly incorporated by reference herein.

Optionally, the system 10 may include a locking member (not shown) for coupling the introducer sheath 20 to the cartridge 120 during use such that subsequent movement of the cartridge 120, e.g., proximally during retraction, causes the introducer sheath 20 to be pulled or otherwise moved along with the cartridge 120. This coupling may prevent accidental proximal movement of the cartridge 120 independent of the introducer sheath 20, which may otherwise result in deploying the sealant 2 from the cartridge 120 within the introducer sheath 20, rather than within a puncture itself. Exemplary embodiments of locking elements that may be used are disclosed in co-pending U.S. patent application Ser. No. 11/864,835, incorporated by reference above.

Turning to FIGS. 3A-5, the housing 148 on the positioning member 140, shown in FIG. 1A, may include a tension indicator assembly 400, e.g., provided around or otherwise carried by the cylinder 416. The tension indicator assembly 400 may be configured to provide a visual cue indicating that a desired amount of tension is being applied by the positioning member 140 during use. For example, during retraction of the positioning member 140, the tension indicator assembly 140 may indicate when an optimum amount of tension is being applied against a vessel wall by the expanded positioning element 146 (shown in FIG. 5), e.g., sufficient to seal the vessel from the puncture, as discussed in further detail below.

The tension indicator assembly 400 may include a two-piece housing, including a proximal housing portion 148a and a distal housing portion 148b, surrounding the cylinder 416. Optionally, the proximal housing portion 148a may be shaped to provide a handle to facilitate manipulating the positioning member 140 and/or to facilitate pulling the proximal housing portion 148a away from the distal housing portion 148b during use. The distal housing portion 148b may be substantially fixed relative to the cylinder 416, and the proximal housing portion 148a may be movable proximally away from or otherwise relative to the distal housing portion 148b (and consequently the cylinder 416 and other portions of the positioning member 140), yet biased to return towards the distal housing portion 148b.

As shown in FIGS. 3A-5, each of the proximal and distal housing portions 148a, 148b may be formed from multiple components that are attached together, such as injection molded plastic covers or sleeves. For example, the proximal housing portion 148a may include two half-covers that may be attached along opposing edges, e.g., using one or more cooperating connectors, adhesives, sonic welding, fusing, and the like. Similarly, the distal housing portion 148b may also include two half-covers that may be attached together. The two half-covers for the distal housing portion 148b may include two half-cylinders extending therefrom that define a cylindrical sleeve 410 when the half-covers of the distal housing portion 148b are attached together. Alternatively, the half-cylinders of the cylindrical sleeve 410 may be separate components that are attached to the half-covers of the distal housing portion 148b, e.g., using one or more cooperating connectors (such as a semi-annular tab on the half-cylinders that may be received in corresponding semi-annular slots in the half-covers, not shown), adhesives, sonic welding, fusing, and the like. In this alternative, the half-cylinders of the cylindrical sleeve may be made from a material that contrasts with the material of the half-covers of the distal housing portion, e.g., a contrasting color.

The cylindrical sleeve 410 may be sized such that the proximal housing portion 148a may be slidably disposed around the cylindrical sleeve 410, as described further below. Optionally, the cylindrical sleeve 410 and/or proximal housing portion 148a may include one or more features for limiting movement of the proximal housing portion 148a relative to the cylinder 410 (and consequently relative to the distal housing portion 148b). For example, as best seen in FIG. 5, the cylindrical sleeve 410 may include a rail 412 or other track, e.g., a groove (not shown) and/or tab 414 integrally molded or otherwise formed with the cylindrical sleeve 410. A rail 412 and tab 414 may be provided on one or both sides of the cylindrical sleeve 410 (the lower rail and tab not being visible in FIG. 5) The proximal housing portion 148a may include a shoulder 408 contoured to slidably fit around the cylindrical sleeve 410 and the shoulder 408 may include one or more slots 409 sized to slidably receive the respective rails 412 therein. Alternatively, the shoulder 408 may include one or more alternative features, e.g., tabs, grooves, and the like (not shown) corresponding to the track(s) on the cylindrical sleeve 410. For example, the rails 410 and slots 409 may allow the proximal housing portion 148a to slide substantially axially relative to the cylindrical sleeve 410 and distal housing portion 148b without substantial rotation around the cylindrical sleeve 410.

Figure 3A:
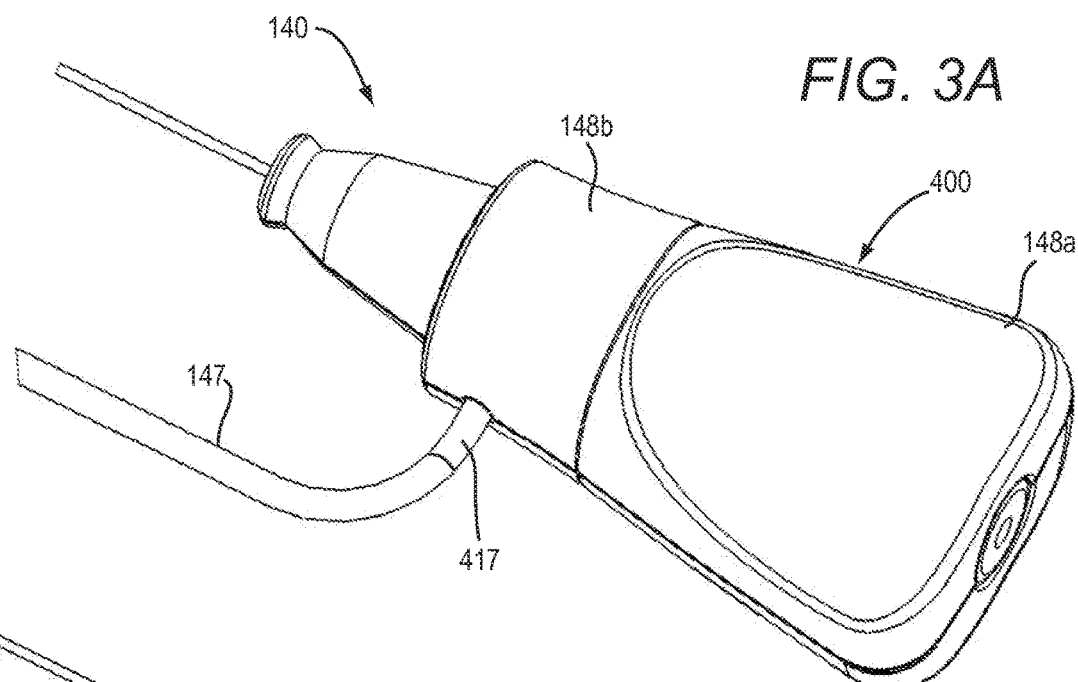
FIGS. 3A and 3B are perspective views of a tension indicator assembly with a spring in a relatively relaxed state and with the housing attached and with a portion of the housing removed to show internal components, respectively.
Figure 3B:
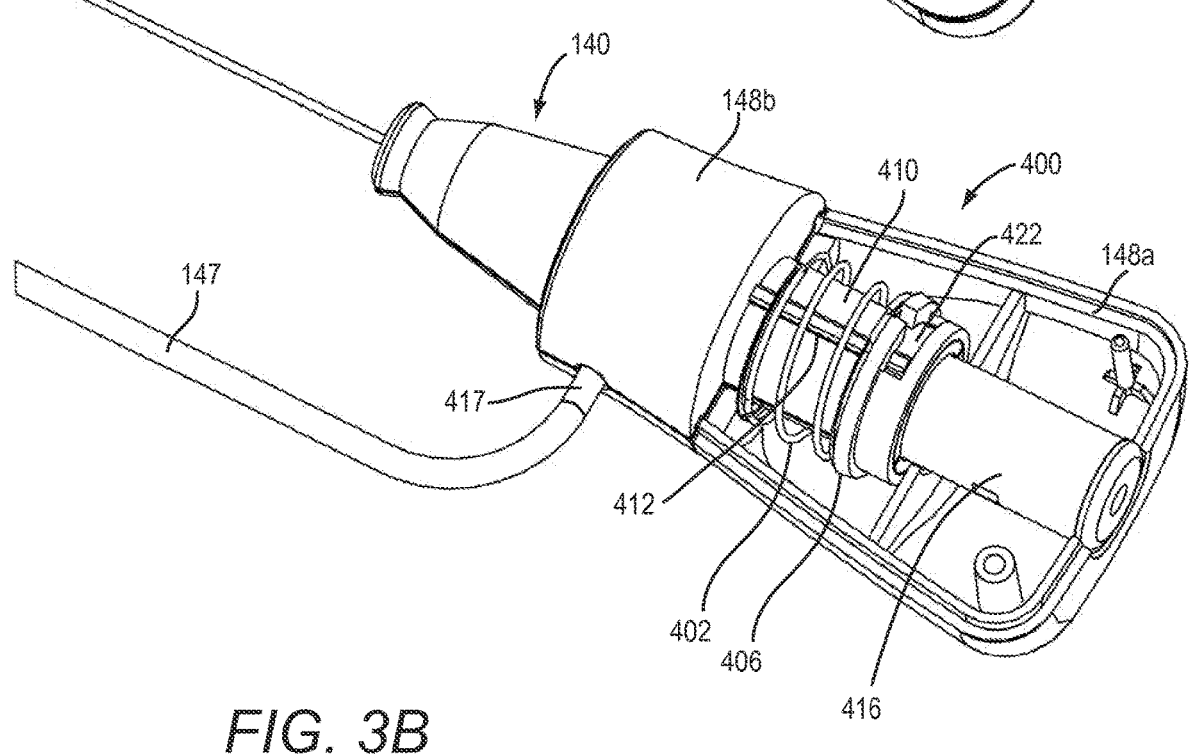
Figure 4A:
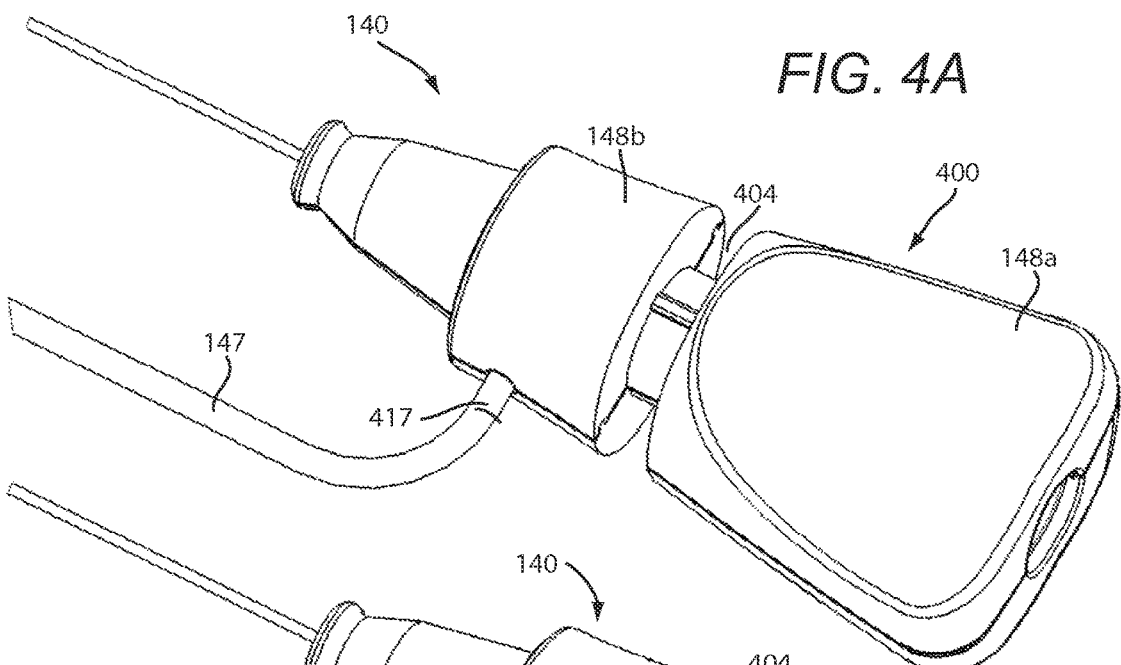
FIGS. 4A and 4B are perspective views of the tension indicator assembly of FIGS. 3A and 3B with the spring in a compressed state and with the housing attached and a portion of the housing removed, respectively.
Figure 4B:
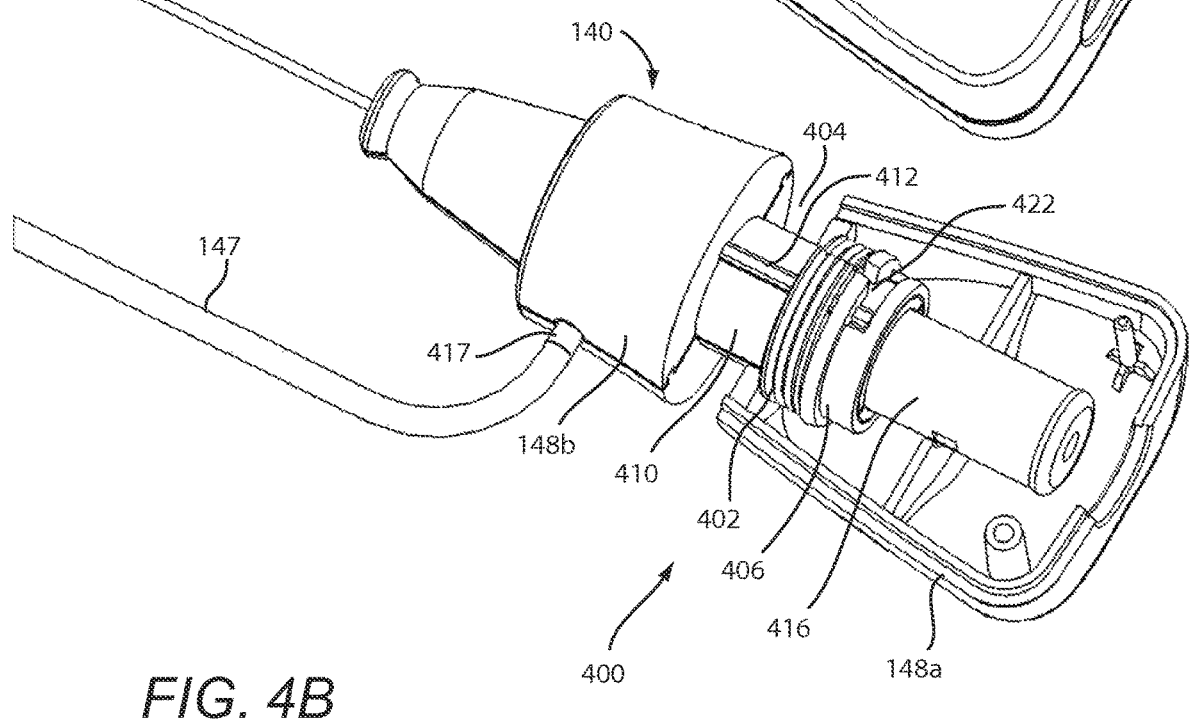

A spring or other biasing element 402 (see FIGS. 3B, 4B and 5) may be coupled to the proximal and distal housing portions 148a, 148b. A visual cue may be provided by the space 404 created by the separation of the two housing portions 148a, 148b of the housing 148, as shown in FIGS. 4A and 4B. When tension is not applied, the spring 402 is in a first position or relatively relaxed state, such as in a pre-loaded state (e.g., where the spring 402 is slightly compressed). Pre-loading the spring 402 may provide a desired force to bias the proximal and distal housing portions 148a, 148b together, as shown in FIGS. 3A and 3B. The spring rate or constant of the spring 402 may be selected such that a force sufficient to compress the spring 402 to a desired extent (e.g., to substantially completely compress the spring 402) is slightly less than a desired tension force applied by the positioning member 140 during use, e.g., slightly less than the tension that would otherwise cause vessel tenting, as explained further below.

For example, when the desired amount of tension is applied between the proximal and distal ends 142, 144 of the positioning member 140, the spring 402 may compress, allowing the proximal and distal housing portions 148a, 148b to separate from one another, as shown in FIGS. 4A and 4B. The space 404 between the proximal and distal housing portions 148a, 148b that results when the spring 402 is compressed may serve as the visual cue to the user that the desired amount of tension is being applied. Optionally, the exposed region within the space 404 may include one or more colors, text, and/or other visual markers (not shown), e.g., a contrasting color to the color of the housing portions 148a, 148b, that may enhance observation of the space 404 as the housing portions 148a, 148b separate.

In the embodiment shown, the spring 402 is a compression spring that is initially in a first position corresponding to a relatively relaxed state (shown in FIGS. 3A and 3B), e.g., a pre-loaded state (with the compressed length equal to the distance set by the spring retaining ring 406 and the shoulder 408 of the proximal housing portion 148a) and is compressible to a higher potential energy state in a second, relatively compressed position (shown in FIGS. 4A and 4B) when a load is applied. Alternatively, instead of the compression spring 402, the tension indicator assembly 400 may include other spring arrangements or biasing mechanisms, such as an extension spring, leaf spring, coil spring, and the like (not shown), e.g., that may be in a lower potential energy state when the proximal and distal housing portions 148a, 148b contact or are closer to one another and in higher potential energy state when a load is applied to separate or otherwise move the proximal and distal housing portions 148a, 148b away from one another.

As shown in FIGS. 3A-5, the spring 402 of the tension indicator assembly 400 is disposed in the proximal housing portion 148a between a spring retaining ring 406 and the shoulder 408 of the proximal housing portion 148a. The spring 402 surrounds the cylinder 416 and cylinder 410, and the spring retaining ring 406 is fixedly attached to the cylindrical sleeve 410 so that a proximal end 402a of the spring 402 is essentially stationary relative to the cylindrical sleeve 410 and a distal end 402b of the spring 402 is free to move along the cylindrical sleeve towards the proximal end 402a of the spring 402. For example, the spring retaining ring 406 may include a slot 422 that receives the tab 414 on the cylindrical sleeve 410, thereby attaching the spring retaining ring 406 to the cylindrical sleeve 410 during assembly. The distal housing portion 148b is fixedly coupled to the cylinder 416 so that when the proximal housing portion 148a is separated or otherwise proximally refracted away from the distal housing portion 148b, i.e., when the spring bias is overcome, the distal housing portion 148b and the cylinder 416 remain substantially stationary relative to one another, thereby causing the separation of the proximal housing portion 148a and the distal housing portion 148b.

The distal housing portion 148b may be attached to the cylinder 416 in any manner. In the embodiment shown in FIGS. 3A-5, the distal housing portion 148b includes a cavity or recess sized to receive the cylinder 416 therein, e.g., such that the port 417 prevents relative axial and/or rotational movement of the cylinder 416 relative to the distal housing portion 148b. Optionally, the port 417 may extend through an opening in the distal housing portion 148b, as shown in FIGS. 3A and 3B, thereby further fixing the cylinder 416 relative to the distal housing portion 148b. Alternatively or in addition, the cylinder 416 may be attached to the cylindrical sleeve 410 and/or other components of the distal housing portion 148b, e.g., by bonding with adhesive, interference fit, sonic welding, cooperating connectors, and the like.

With continued reference to FIGS. 3A-5, to make the tension indicator assembly 400, the components are made, e.g., as described above, and assembled together. For example, the components of the distal housing portion 148b may be attached together around the cylinder 416. The spring 402 may then be disposed around the cylindrical sleeve 410, and the spring retaining ring 406 may be slid over the cylinder 416 and then over the cylindrical sleeve 410 until the tab(s) 414 on the cylindrical sleeve 410 are captured in the slot(s) 422 in the spring retaining ring 406. Alternatively, the cylindrical sleeve 410 and/or spring retaining ring may be integrally molded or otherwise formed as part of the cylinder 416.

The components of the proximal housing portion 148a are then attached together around the cylinder 416 and cylindrical sleeve 410, e.g., such that the cylindrical sleeve 410 is encircled by the shoulder 408 of the proximal housing portion 148a and the hollow cylinder 410 extends into the proximal housing portion 148a when the spring 402 is in the relatively relaxed state. As described above, the proximal housing portion 148a, including the shoulder 408 and any other components, may be integrally molded or otherwise formed, e.g., as halves that may be attached together and/or slidably attached around the cylinder 416. Thus, the hollow cylinder 410 and the cylinder 416 coupled thereto are configured to slide in and out of the proximal housing portion 148a through an opening created by the shoulder 408 while the spring 402 remains within the proximal housing portion 148a between the shoulder 408 and the spring retaining ring 406.

Turning to FIGS. 6A-10B, an exemplary method is shown for sealing a puncture 90, e.g., using the system 10 described above to deliver a sealant 2, e.g., to achieve hemostasis within the puncture 90. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

Figure 6A:
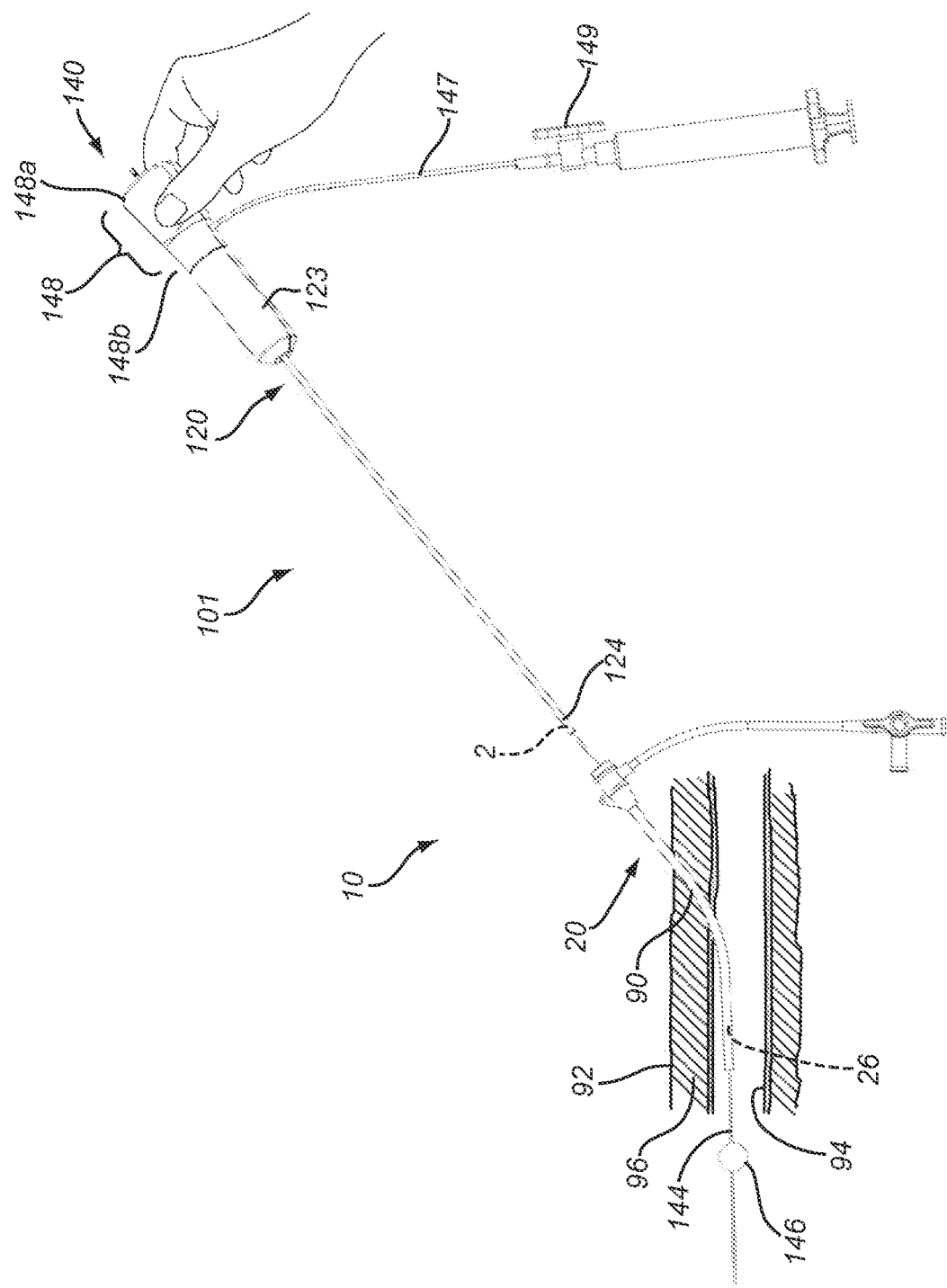
Figure 6B:
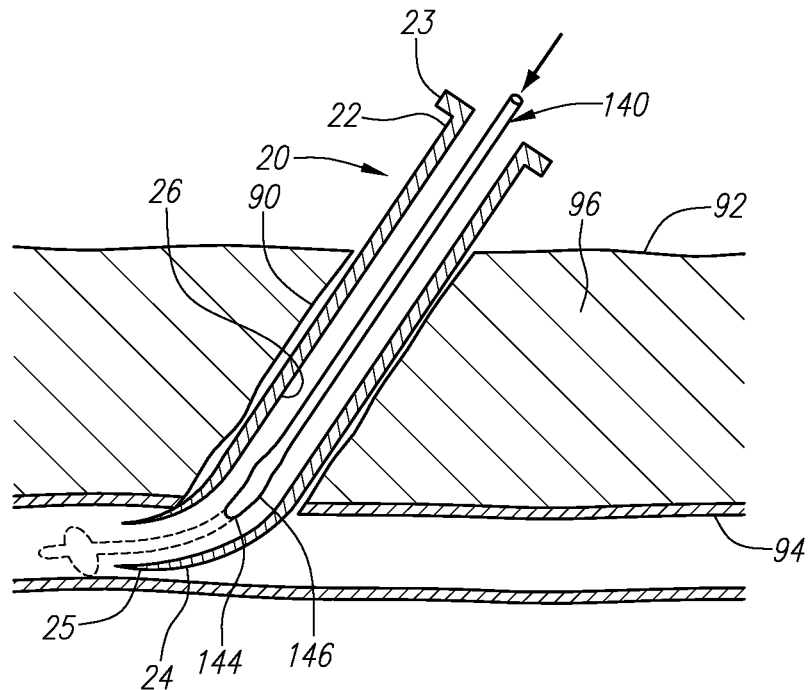
FIGS. 6B, 7B, 8B, 9B, and 10B are cross-sectional details of the method of FIGS. 6A, 7A, 8A, 9A, 10A.

In an exemplary method, the puncture 90 may be created using known procedures, e.g., using a needle, guidewire, one or more dilators, and the like (not shown). Then, as depicted in FIGS. 6A and 6B, an introducer sheath 20 may be advanced through the puncture 90 into the vessel 94, e.g., over a guide wire (not shown) placed through the puncture 90 into the vessel 94. The introducer sheath 20 may provide access into the vessel 94 for one or more instruments, e.g., to allow one or more diagnostic and/or interventional procedures to be performed via the vessel 94. Upon completing the procedure(s) via the vessel 94, any such instrument(s) may be removed from the puncture 90, leaving the introducer sheath 20 extending through the puncture 90 into the vessel 94.

The distal end 144 of the positioning member 140 may be introduced into the puncture 90, e.g., through the lumen 26 of the introducer sheath 20, with the expandable positioning element 146 in a collapsed condition, as shown in FIG. 6B. As shown in FIG. 6A, the cartridge 120, along with the sealant 2 and pusher member 130 (not shown in FIG. 6A for clarity, see FIGS. 1A-2B), may be provided initially on the proximal end of the positioning member 140, e.g. near the positioning member housing 148. Thus, the distal end 124 of the cartridge 120 may initially be located outside the puncture 90 when the positioning member 140 is advanced into the puncture 90. Alternatively, the cartridge 120 may be carried on the distal end 144 of the positioning member 140, e.g., as shown in FIG. 2B, such that the cartridge 120 (along with the sealant 2 and pusher member 130) are introduced simultaneously with the positioning member 140, as described in co-pending U.S. patent application Ser. No. 11/854,534, incorporated by reference herein.

Still referring to FIGS. 6A and 6B, the distal end 144 of the positioning member 140 may be inserted through the puncture 90 (via the introducer sheath 20) and into the vessel 94. Optionally, the positioning member 140 may include one or more markers (not shown) that may be disposed adjacent the proximal end 22 of the introducer sheath 20 when the distal end 144 extends beyond the distal end 24 of the introducer sheath 20. Once the positioning element 146 is disposed within the vessel 94, i.e., beyond the distal end 24 of the introducer sheath 20, the positioning element 146 may be expanded to an enlarged condition, as shown in FIG. 6A and as shown in phantom in FIG. 6B. After expanding the positioning element 146, the positioning member 140 may be at least partially withdrawn until the positioning element 146 contacts the wall of the vessel 94, e.g., to substantially seal the vessel 94 from the puncture 90.

Figure 7B:
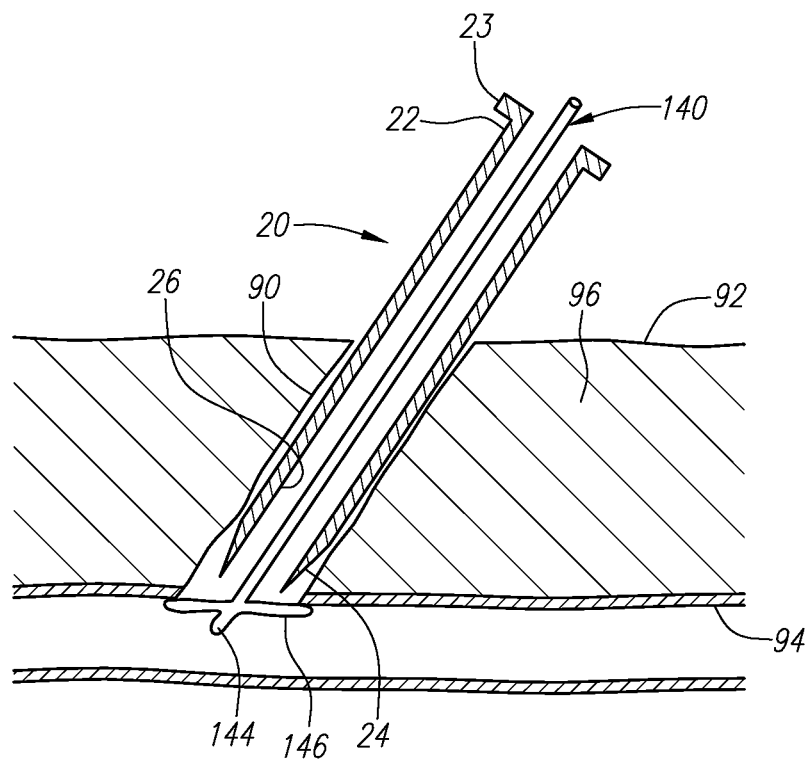

In an exemplary method, this may involve a two-step process (although it may be completed in a single, substantially continuous action). First, with the positioning element 146 expanded within the vessel 94, as shown in FIG. 6A and in phantom in FIG. 6B, the positioning member 140 may be withdrawn until the positioning element 146 contacts the distal end 24 of the introducer sheath 20, which may provide a first tactile feedback to the user (i.e., that the positioning element 146 has contacted the introducer sheath 20, e.g., based upon the increased weight and/or resistance to proximal movement). After encountering the first tactile feedback, the positioning member 140 may be withdrawn further until the positioning element 146 contacts the wall of the vessel 94 and resists further withdrawal, thereby providing a second tactile feedback. The introducer sheath 20 may be pulled proximally by the positioning element 146 as the positioning member 140 is withdrawn, e.g., until the positioning element 146 contacts the wall of the vessel 94 and the distal end 24 of the introducer sheath 20 is withdrawn from the vessel 94 into the puncture 90, as shown in FIGS. 7A and 7B.

The tension indicator apparatus 400 may facilitate confirming that excessive force is not applied by the positioning element 146 to the vessel 94, e.g., by identifying that an optimal amount of tension is being applied by the positioning member 140, e.g., during deployment of the sealant 2. For example, if the positioning member 140 is withdrawn with excessive force after the positioning element 146 contacts the wall of the vessel 94, the wall of the vessel 94 may tent, which may cause damage to the wall of the vessel 94, and/or may cause ineffective or inaccurate sealing of the vessel 94. Conversely, if too little tension is applied, the vessel 94 may not be properly sealed from the puncture 90 and/or the sealant 2 may be deployed improperly, e.g., into the vessel 94. It may be desirable to provide additional indicators to the user in addition to using the first and second tactile feedback during withdrawal of the positioning member 140 because detection of the feedback depends on the tactile sensitivity of the user, which may be inaccurate.

Thus, the tension indicator assembly 400 may provide more accurate tension control, which may be calibrated by setting the spring constant of the spring 402 (not shown, see, e.g., FIG. 5). The desired amount of tension applied by the positioning member 140 may ensure that there is sufficient force between the positioning element 146 and the wall of the vessel 94 to substantially seal the vessel 94, e.g., while avoiding tenting, and/or facilitating proper positioning of the sealant 2. The force corresponding to the desired tension may be slightly greater than the force required to compress the spring 402 in the tension indicator assembly 400. During proximal retraction of the positioning member 140, the proximal housing portion 148a separates from the distal housing portion 148b when the desired amount of tension on the positioning member 140 is achieved. Thus, the separation of the proximal and distal housing portions 148a, 148b may indicate that proximal retraction of the positioning member 140 should be maintained at that force and not increased, since further retraction may cause tenting of the vessel 94. The space 404 between the proximal and distal housing portions 148a, 148b and/or appearance of the cylindrical sleeve 410 may serve as a visual cue that the desired amount of proximal tension is being applied to the positioning member 140, e.g., for accurate deployment of the sealant 2. The desired amount of proximal tension may be maintained manually or using a tension device (not shown) to provide temporary hemostasis, e.g., during the subsequent steps. Exemplary tension devices are disclosed in co-pending U.S. patent application Ser. No. 10/806,952, filed Mar. 22, 2004 and published as US 2004/0267308, the entire disclosure of which is expressly incorporated herein by reference.

Figure 7A:
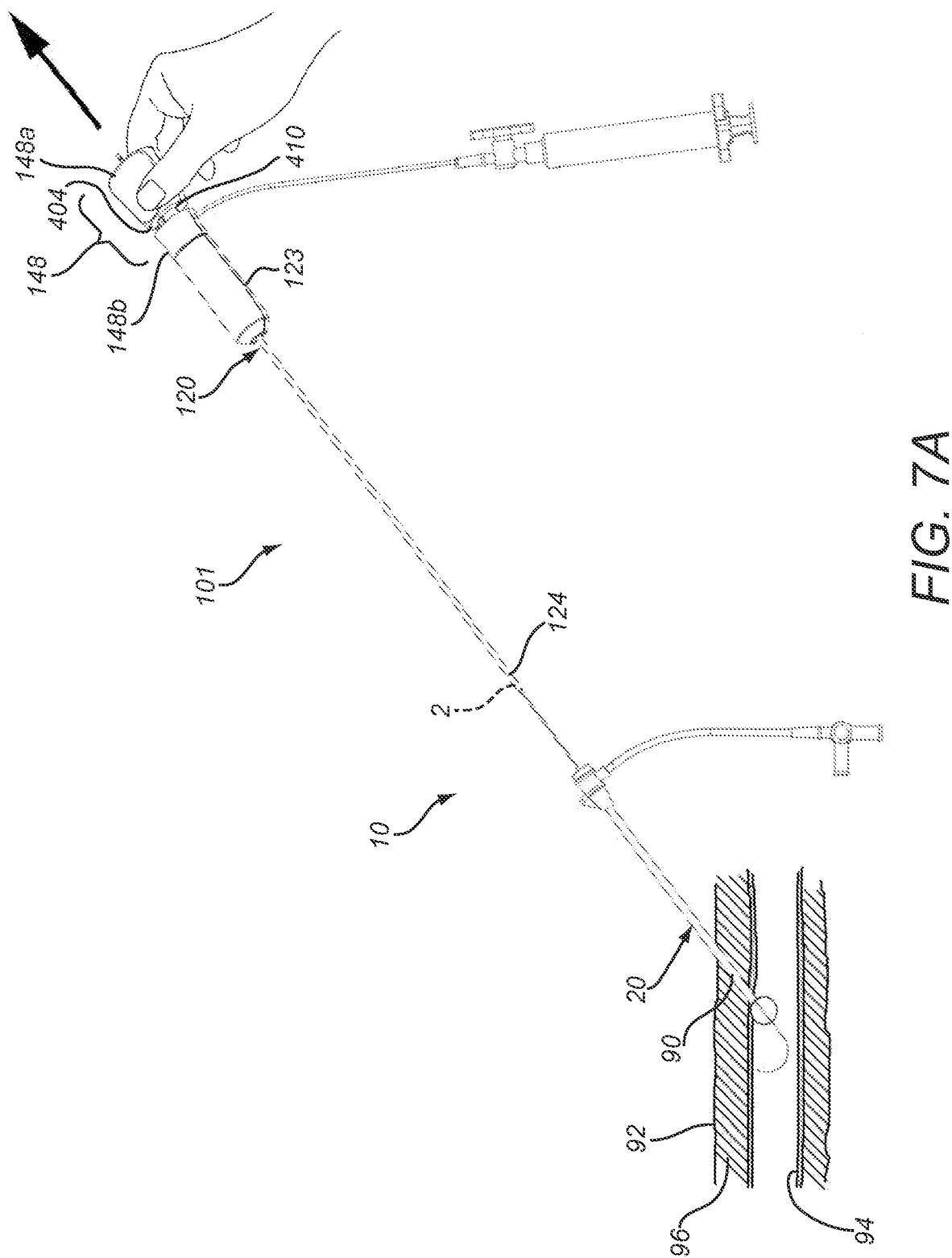

Thus, as shown in FIG. 7A, the positioning member 140 has been proximally retracted by pulling on the proximal housing portion 148a, as indicated by arrow 162, until separation between the proximal and distal housing portions 148a, 148b occurs, indicating that a desired amount of proximal tension is being applied to the positioning member 140 to accurately seal the vessel 94 from the puncture 90.

Figure 8B:
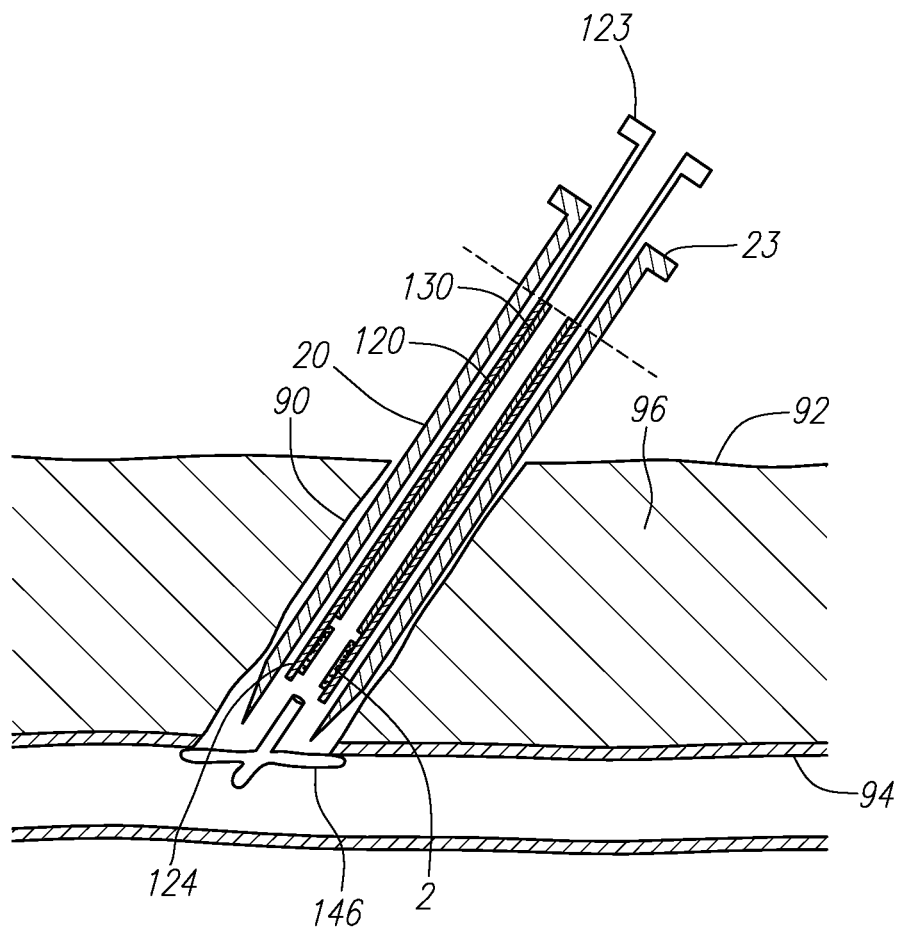

Turning to FIGS. 8A and 8B, the cartridge 120 (carrying the sealant 2, shown in FIG. 8B) may then be advanced distally over the positioning member 140 into the puncture 90, as indicated by arrow 164. For example, FIG. 8A illustrates the cartridge 120 being advanced distally over the positioning member 140 and into the introducer sheath 20. The cartridge 120 may be further advanced into the introducer sheath 20 until the distal end 124 of the cartridge 120 contacts the positioning element 146, as shown in FIG. 8B.

In one embodiment, the cartridge 120 (and sealant 2) may be advanced through the introducer sheath 20 until a hub 123 of the cartridge 120 abuts a hub 23 on the introducer sheath 20. In another embodiment, the cartridge 120 may be advanced until a locking element (not shown) engages, thereby coupling the cartridge 120 to the introducer sheath 20.

Figure 9A:
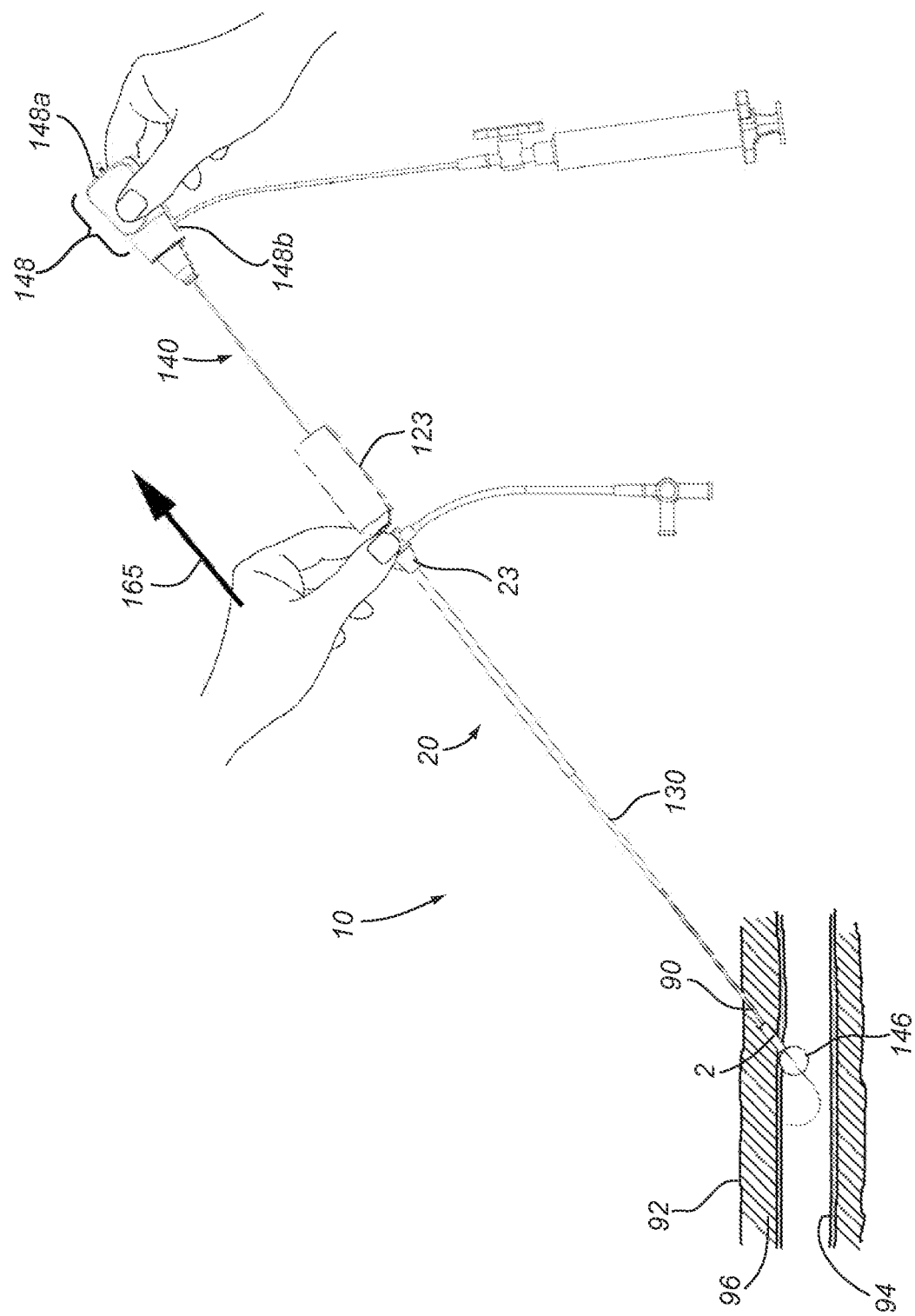
Figure 9B:
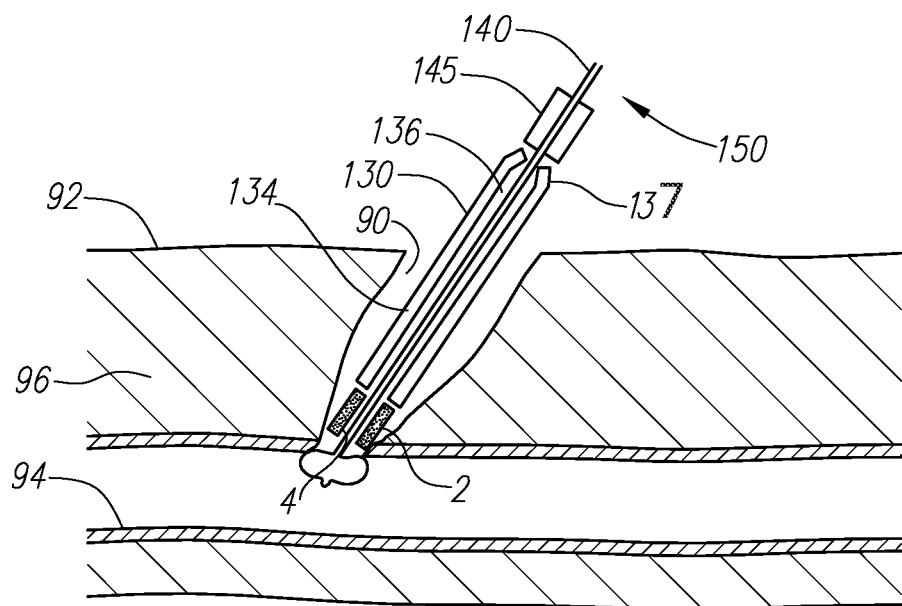

Once the sealant 2 is in the desired position within the puncture 90 (shown in FIG. 8B), the housing 148 may be released (shown in FIG. 9A), causing the spring 402 (not shown in FIG. 9A for clarity, see FIGS. 3B, 4B and 5) to return to its first position, i.e., pre-loaded, relatively relaxed state, thereby forcing the proximal and distal housing portions 148a, 148b together. The cartridge 120 may be retracted, e.g., by pulling proximally on the hub 23 of the sheath 20 and/or the hub 123 of the cartridge 120, as indicated by arrow 165 in FIG. 9A. For example, if the optional locking element (not shown) has coupled the introducer sheath 20 to the cartridge 120, pulling the hub 123 also withdraws the introducer sheath 20 from the puncture 90. Alternatively, the introducer sheath 20 may be pulled, thereby withdrawing the cartridge 120 along with the introducer sheath 20. As the cartridge 120 is retracted, the pusher member 130 may prevent substantial proximal movement of the sealant 2, thereby exposing the sealant 2 within the puncture 90, as shown in FIG. 9B. For example, as described above with reference to FIGS. 2A and 2B, as the cartridge 120 is advanced, the pusher member 130 may pass over the raised element 145 of the positioning member 140, as shown in FIG. 2B. When the cartridge 120 is then retracted, the latch element 137 on the pusher member 130 may abut the raised element 145, thereby preventing substantial proximal movement of the pusher member 130 and the sealant 2 adjacent the distal end 134 of the pusher member 130.

When the sealant 2 is exposed within the puncture 90, the sealant 2 may be exposed to blood and/or other body fluids within the puncture 90. This exposure may cause the sealant 2 to absorb fluid and/or otherwise expand within the puncture 90, e.g., to provide hemostasis. If desired, once the sealant 2 is exposed within the puncture 90, the pusher member 130 may be advanced to compress or tamp the sealant 2, e.g., against the positioning element 146, as depicted by arrow 166 in FIG. 10A. Optionally, the positioning member 140 may include one or more distance markers 143 adjacent the proximal end 132 (after the cartridge 120 and pusher member 130 are advanced), and the pusher member 130 may be advanced into the puncture 90 a desired distance, which may be confirmed by monitoring the distance markers 143. Optionally, during tamping, the proximal housing portion 148a may be pulled until the proximal housing portion 148a separates from the distal housing portion 148b to maintain the seal between the positioning element 146 and the wall of the vessel 94 while the sealant 2 is compressed.

Figure 10B:
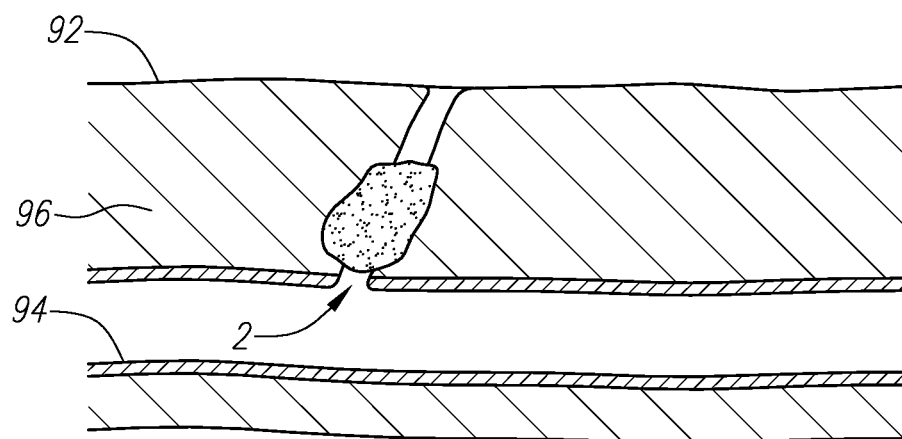
Figure 10A:
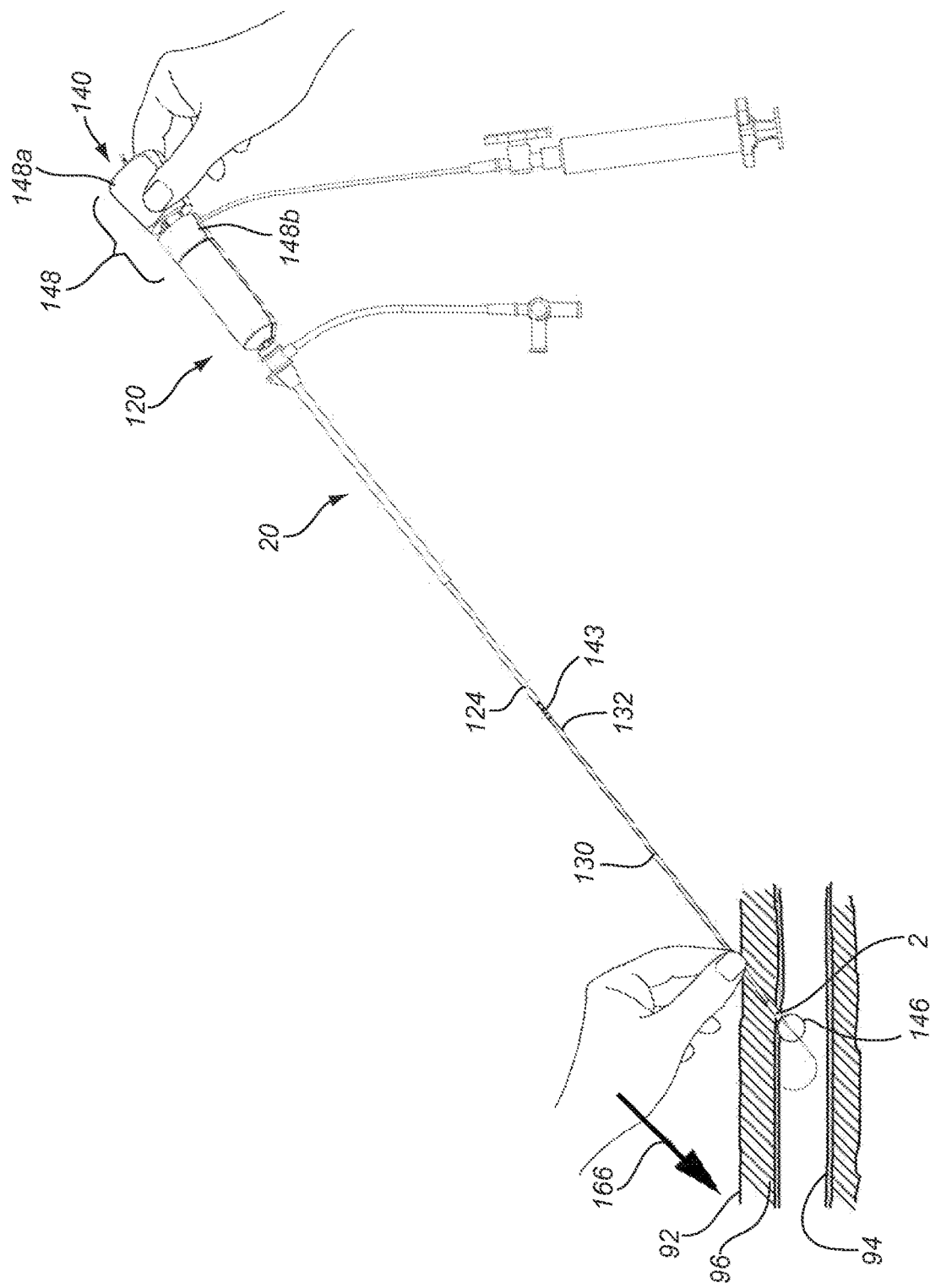

Once the sealant 2 has been exposed for sufficient time and/or tamped by the pusher member 130, the positioning element 146 may be collapsed, and the positioning member 140 withdrawn from the vessel 94 and puncture 90, e.g., by pulling the collapsed positioning element 146 through the sealant 2 and pusher member 130. The pusher member 130 may be maintained substantially stationary during withdrawal of the positioning member 140, e.g., to prevent migration and/or dislodgment of the sealant 2 within the puncture 90. Once the positioning member 140 is completely removed, the pusher member 130 may be removed from the puncture 90, leaving the sealant 2 within the puncture 90, as shown in FIG. 10B.

Optionally, after removing the positioning member 140, liquid hydrogel or other sealing compound, or other material may be delivered into the puncture 90, e.g., above and/or around the sealant 2, to assist in achieving hemostasis. For example, such material may be delivered via the lumen 136 of the pusher member 130 and/or by introducing another delivery device (not shown) into the puncture 90, e.g., after removing the pusher member 130. In another alternative, the cartridge 120 and sealant 2 may be eliminated, and the positioning member 140 may be used to substantially seal the puncture 90 from the vessel 94 temporarily. In this alternative, other sealants may then be delivered into the puncture 90, if desired, whereupon the positioning member 140 may be removed, as described above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for sealing a puncture extending through tissue to a body lumen, comprising:
   introducing a distal end of an elongate member through the puncture until a positioning element on the distal end is disposed within the body lumen;
   introducing a tubular member simultaneously with the elongate member, the tubular member comprising a lumen through which the elongate member is positioned and a sealant positioned within the tubular member at a distal end thereof proximate the positioning element;
   deploying the positioning element within the body lumen;
   retracting the elongate member until the deployed positioning element contacts a wall of the body lumen adjacent the puncture and a tension indicator indicates that a desired tension is being applied by the positioning element to the wall of the body lumen; and
   retracting the tubular member at least partially from the puncture to expose at least a portion of the sealant within the puncture distally beyond the tubular member.

2. The method of claim 1, wherein the positioning element is an expandable balloon.

3. The method of claim 1, further comprising:
   introducing an introducer sheath into the puncture prior to introducing the distal end of the elongate member through the puncture; and,
   wherein the distal end of the elongate member is introduced through the puncture by introducing the distal end of the elongate member through the introducer sheath.

4. The method of claim 1, wherein retracting the tubular member further comprises holding the sealant proximate the positioning element with a pusher member positioned within the tubular member.

5. The method of claim 4, further comprising advancing the pusher member toward the positioning element to compress the sealant at least partially within the puncture.

6. The method of claim 5, further comprising:
   collapsing the positioning element; and,
   removing the positioning element from the puncture, thereby withdrawing the collapsed positioning element through the sealant.

7. The method of claim 1, wherein retracting the positioning element further comprises separating a first housing portion of the tension indicator from a second housing portion of the tension indicator.

8. The method of claim 7, wherein the first housing portion of the tension indicator is a proximal housing portion of the tension indicator and wherein the second housing portion of the tension indicator is a distal housing portion of the tension indicator.

9. The method of claim 7, wherein the first housing portion of the tension indicator is fixed to a proximal end of the positioning element.

10. The method of claim 7, wherein the tension indicator comprises a spring, and wherein separating the first housing portion of the tension indicator from the second housing portion of the tension indicator further comprises overcoming a biasing force of the spring.

11. The method of claim 1, wherein the tension indicator indicates that sufficient contact force is being applied to the wall of the body lumen by the deployed positioning element to seal the body lumen from the puncture.

12. The method of claim 1, wherein the tension indicator provides a visual cue that a predetermined contact force is being applied to the wall of the body lumen by the deployed positioning element.

13. The method of claim 12, wherein the visual cue includes at least one color, text or other visual marker.

14. The method of claim 1, further comprising:
   collapsing the positioning element; and,
   removing the positioning element from the puncture, thereby withdrawing the collapsed positioning element through the sealant.

15. The method of claim 1, wherein the tubular member is advanced until the sealant is disposed adjacent the positioning element, the method further comprising releasing the tension on the tension indicator before retracting the tubular member to expose the sealant within the puncture.

16. The method of claim 1, wherein the tubular member is advanced until the sealant is disposed adjacent the positioning element, the method further comprising maintaining the tension on the tension indicator before retracting the tubular member to expose the sealant within the puncture.

17. A method for sealing a puncture extending through tissue to a body lumen, comprising:
   introducing a distal end of an elongate member through the puncture until a positioning element on the distal end is disposed within the body lumen;
   deploying the positioning element within the body lumen; and
   retracting the elongate member until the deployed positioning element contacts a wall of the body lumen adjacent the puncture and a tension indicator indicates that a desired tension is being applied by the positioning element to the wall of the body lumen, wherein retracting the positioning element further comprises separating a first housing portion of the tension indicator from a second housing portion of the tension indicator.

18. The method of claim 17, wherein the first housing portion of the tension indicator is a proximal housing portion of the tension indicator and wherein the second housing portion of the tension indicator is a distal housing portion of the tension indicator.

19. The method of claim 17, wherein the first housing portion of the tension indicator is fixed to a proximal end of the positioning element.

20. The method of claim 17, wherein the tension indicator comprises a spring, and wherein separating the first housing portion of the tension indicator from the second housing portion of the tension indicator further comprises overcoming a biasing force of the spring.

21. A method for sealing a puncture extending through tissue to a body lumen, comprising:
- introducing a distal end of an elongate member through the puncture until a positioning element on the distal end is disposed within the body lumen;
- deploying the positioning element within the body lumen;
- retracting the elongate member until the deployed positioning element contacts a wall of the body lumen adjacent the puncture and a tension indicator indicates that a desired tension is being applied by the positioning element to the wall of the body lumen;
- advancing a tubular member carrying a sealant along the elongate member and through the introducer sheath; and,
- retracting the tubular member and the introducer sheath at least partially from the puncture to expose at least a portion of the sealant within the puncture distally beyond the introducer sheath.

22. The method of claim 21, further comprising:

collapsing the positioning element; and, removing the positioning element from the puncture, thereby withdrawing the collapsed positioning element through the sealant.

23. The method of claim 21, wherein the tubular member is advanced until the sealant is disposed adjacent the positioning element, the method further comprising releasing the tension on the tension indicator before retracting the tubular member to expose the sealant within the puncture.

24. The method of claim 21, wherein the tubular member is advanced until the sealant is disposed adjacent the positioning element, the method further comprising maintaining the tension on the tension indicator before retracting the tubular member to expose the sealant within the puncture.

* * * * *